US008470986B2

(12) United States Patent
Shoda et al.

(10) Patent No.: US 8,470,986 B2
(45) Date of Patent: Jun. 25, 2013

(54) METHOD FOR PRODUCTION OF SUGAR OXAZOLINE DERIVATIVE

(75) Inventors: Shinichiro Shoda, Sendai (JP); Atsushi Kobayashi, Sendai (JP); Masato Noguchi, Sendai (JP); Tomonari Tanaka, Sendai (JP); Hidetoshi Gyakushi, Sendai (JP)

(73) Assignee: Tohoku University (JP)

( * ) Notice: Subject to any disclaimer, the term of this patent is extended or adjusted under 35 U.S.C. 154(b) by 205 days.

(21) Appl. No.: 12/528,547

(22) PCT Filed: Mar. 7, 2008

(86) PCT No.: PCT/JP2008/054194
§ 371 (c)(1),
(2), (4) Date: Aug. 25, 2009

(87) PCT Pub. No.: WO2008/111526
PCT Pub. Date: Sep. 18, 2008

(65) Prior Publication Data
US 2010/0121041 A1     May 13, 2010

(30) Foreign Application Priority Data
Mar. 9, 2007   (JP) ................................. 2007-059478

(51) Int. Cl.
*C07H 17/02* (2006.01)

(52) U.S. Cl.
USPC ..................................................... 536/18.7

(58) Field of Classification Search
None
See application file for complete search history.

(56) References Cited

U.S. PATENT DOCUMENTS

2004/0176588 A1 * 9/2004 Shoda et al. ................. 536/55.3

FOREIGN PATENT DOCUMENTS

| JP | 9-3088 | 1/1997 |
| JP | 2003-12683 | 1/2003 |

OTHER PUBLICATIONS

Song et al. Organic Letters 2006, vol. 8, No. 14, 3081-3084.*
Isobe, J. Org. Chem. 1999, 64, 6984-6988.*
Isobe, J. Org. Chem. 1999, 64, 6989-6992.*
Kobayashi et al. J. Am. Chem. Soc. 1996, 118, 13113-13114.*
Umekawa et al. The Journal of Biological Chemistry, 283, 4469-4479, published Dec. 20, 2007.*
S. Shoda et al., *Helv. Chim. Acta*, 85, 3919 (2002), "Efficient Method for the Elongation of the N-Acetylglucosamine Unit by Combined Use of Chitinase and β-Galactosidase".
Bing Li et al., J. Am. Chem. Soc., 127, 9692 (2005), "Highly Efficient Endoglycosidase-Catalyzed Synthesis of Glycopeptides Using Oligosaccharide Oxazolines as Donor Substrates".
J. Kadokawa et al., "Direct Conversion of 2-Acetamido-2-Deoxysugars to 1, 2-Oxazoline Derivatives by Dehydrative Cyclization in Water" *Heterocycles*, 63(7), (2004), pp. 1531-1535.
H. Gyakushi et al., *Abstracts of the Second Tohoku University Bioscience Symposium*, "One-step synthesis of sugar oxazoline derivatives using a water-soluble carbodiimide," May 2005.
55th Society of Polymer Science Meeting, Title "One-pot polymerization reaction of non-protected sugars by dehydrative condensing agent-enzyme system" M. Noguchi, T. Misawa, M. Ishihara, A. Kobayashi, S. Shoda, Journal name: *Polymer Preprints*, Japan vol. 55, No. 2 (2006), pp. 4826.
2006 Society of Polymer Science Tohoku Branch Research Publications Meeting, Title: "One-pot synthesis of polysaccharides from non-protected sugars by employing enzymatic polymerization reaction," Authors: M. Noguchi, T. Misawa, M. Ishihara, A. Kobayashi, S. Shoda, Journal name: *Abstracts of the 2006 Society of Polymer Science Tohoku Branch Research Publications Meeting*, p. 21.
H. Gyakushi et al., Abstracts of the Third Tohoku Univeristy Bioscience Symposium, "One-pot glycosylation of non-protected sugars," May 2006.
Kimiko AN'No, Nobuko SENO, to Kagaku no Kiso, Kodansha Ltd., 1995, pp. 172 to 174.
Satoru Nakabayashi, Christopher D. Warren, and Roger W. Jeanloz, "A new procedure for the preparation of oligosaccharide oxazolines", Carbohydrate Research, 1986, vol. 150, p. C7-C10.
"A Short, Stereospecific Synthesis of Dihydrooxazoles From Serine and Threonine Derivatives", Tetrahedron Letters, 1992, vol. 33 No. 7, p. 907-910.
Chinese Office Action w/English translation, dated Jun. 3, 2011 (7 pgs).

* cited by examiner

*Primary Examiner* — Layla Bland
(74) *Attorney, Agent, or Firm* — Hayes Soloway P.C.

(57) ABSTRACT

A method for producing an oxazoline derivative from a non-protected sugar in a simple manner and a method for producing a glycoside by utilizing the product of the aforementioned method are disclosed. A sugar oxazoline derivative is synthesized in one step in an aqueous solution from a sugar having a free hemiacetal hydroxy group and an amide group by using a haloformamidinium derivative as a dehydration/condensation agent. A glycoside is produced by using the oxazolidine derivative as a sugar donor and also using a sugar dehydrogenase. The method can be applied to the production of a compound having a long sugar chain, and is therefore useful for a production of a physiologically active oligosaccharide, a carrier for a drug delivery system, a surfactant, a carbohydrate pharmaceutical, a glycopeptide, a glycoprotein, a carbohydrate polymer or the like.

8 Claims, 26 Drawing Sheets

METHOD FOR PRODUCTION OF SUGAR OXAZOLINE DERIVATIVE

TECHNICAL FIELD

The present invention relates to a process for producing an oxazoline derivative which comprises using an unprotected sugar chain as the starting material; a novel compound obtained thereby; and a process for producing a glycoside compound which comprises using the said oxazoline derivative as a sugar donor.

BACKGROUND ART

Recent technological advances have made it clear that sugar chains are involved in a variety of life processes and the importance of sugar-chain compounds has been even more strongly recognized. One method of synthesizing sugar-chain compounds is through an enzyme-catalyzed glycosylation reaction. Glycosylation using a sugar oxazoline derivative as the sugar donor among the enzyme-catalyzed glycosylation reactions is a very useful method of synthesizing glycosides because the glycosylation reaction is an addition reaction and advances without any accompanying elimination of acid, water, or the like. Compounds having an added sugar chain are useful for various purposes, for example, as a bioactive oligosaccharide, carrier of a drug delivery system, surfactant, glycopharmaceutical, glycopeptide, glycoprotein, glycopolymer, and the like.

Sugar derivatives having an activated anomer carbon are known as sugar donors of glycosylation reactions using a glycohydrolase. Sugar oxazoline derivatives among them are a useful substrate as a sugar donor having no leaving groups. However, conventional methods of synthesizing sugar oxazoline derivatives require the use of an organic solvent and include multiple steps, including the protection and deprotection of the hydroxyl groups present in the sugar [S. Shoda et al., *Helv. Chim. Acta,* 85, 3919 (2002) (Non-patent Document 1)]. The synthesis of oxazoline derivatives of oligosaccharides is particularly difficult [Bing Li et al., *J. Am. Chem. Soc.,* 127, 9692 (2005) (Non-patent Document 2)] and is seldom performed today. Conventional methods of synthesizing sugar oxazoline derivatives are also known, as in JP Kokai 9-3088 (Patent Document 1) and JP Kokai 2003-12683 (Patent Document 2). Such conventional chemical synthesis methods involve a complex procedure and are difficult to apply to long sugar chains because they require multiple steps such as protection and deprotection of hydroxyl groups. The development of a technique to simply and moderately synthesize sugar oxazoline derivatives without using steps such as protection and deprotection is consequently desired in sugar chain synthesis From this viewpoint, a method of synthesizing a sugar oxazoline derivative from an unprotected sugar in one step using a water-soluble carbodiimide as a dehydrating agent was developed [J. Kadokawa et al., *Heterocycles,* 63(7), (2004), pp. 1531-1535 (Non-patent Document 3) and H. Gyakushi et al., *Abstracts of the Second Tohoku University Bioscience Symposium,* "One-step synthesis of sugar oxazoline derivatives using a water-soluble carbodiimide," May 2005 (Non-patent Document 4)]. A method of direct synthesis of sugar oxazoline derivatives from unprotected sugars in an aqueous solvent using a triazine derivative as a dehydrating agent has also been developed [55th Society of Polymer Science Meeting, Title: "One-pot polymerization reaction of non-protected sugars by dehydrative condensing agent-enzyme system," Authors: M. Noguchi, T. Misawa, M. Ishihara, A. Kobayashi, S. Shoda, Journal name: *Polymer Preprints,* Japan Vol. 55, No. 2 (2006), pp. 4826 (Non-patent Document 5); 2006 Society of Polymer Science Tohoku Branch Research Publications Meeting, Title: "One-pot synthesis of polysaccharides from non-protected sugars by employing enzymatic polymerization reaction," Authors: M. Noguchi, T. Misawa, M. Ishihara, A. Kobayashi, S. Shoda, Journal name: *Abstracts of the* 2006 *Society of Polymer Science Tohoku Branch Research Publications Meeting,* pp. 21 (Non-patent Document 6); H. Gyakushi et al., Abstracts of the Third Tohoku University Bioscience Symposium, "One-pot glycosylation of non-protected sugars," May 2006 (Non-patent Document 7)].

Patent Document 1: JP Kokai 9-3088 (JP, 9-3088, A1 (1997))
Patent Document 2: JP Kokai 2003-12683 (JP, 2003-12683, A1)
Non-patent Document 1: S. Shoda et al., *Helv. Chim. Acta,* 85, 3919 (2002)
Non-patent Document 2: Bing Li et al., *J. Am. Chem. Soc.,* 127, 9692 (2005)
Non-patent Document 3: J. Kadokawa, M. Mito, S. Takahashi, M. Noguchi, S. Shoda, "Direct Conversion of 2-Acetamido-2-Deoxysugars to 1,2-Oxazoline Derivatives by Dehydrative Cyclization," *Heterocycles,* 63(7), (2004), pp. 1531-1535
Non-patent Document 4: H. Gyakushi, S. Takahashi, M. Shiratori, M. Noguchi, A. Kobayashi, S. Shoda, *Abstracts of the Second Tohoku University Bioscience Symposium,* "One-step synthesis of sugar oxazoline derivatives using a water-soluble carbodiimide," May 2005.
Non-patent Document 5: 55th Society of Polymer Science Meeting, Title: "One-pot polymerization reaction of non-protected sugars by dehydrative condensing agent-enzyme system," Authors: M. Noguchi, T. Misawa, M. Ishihara, A. Kobayashi, S. Shoda, Journal name: *Polymer Preprints,* Japan Vol. 55, No. 2 (2006), p. 4826
Non-patent Document 6: 2006 Society of Polymer Science Tohoku Branch Research Publications Meeting, Title: "One-pot synthesis of polysaccharides from non-protected sugars by employing enzymatic polymerization reaction," Authors: M. Noguchi, T. Misawa, M. Ishihara, A. Kobayashi, S. Shoda, Journal name: *Abstracts of the* 2006 *Society of Polymer Science Tohoku Branch Research Publications Meeting,* pp. 21
Non-patent Document 7: H. Gyakushi et al., Abstracts of the Third Tohoku University Bioscience Symposium, "One-pot glycosylation of non-protected sugars," May 2006

DISCLOSURE OF THE INVENTION

Problems to be Solved by the Invention

A problem has been that the procedure is complex and difficult to apply to long sugar chains when a conventional synthesis method that requires multiple steps such as protection and deprotection of the hydroxyl groups is used to synthesize an oxazoline derivative that is useful as a sugar donor when enzymatically synthesizing a glycoside. There is also a method of synthesis that employs a Lewis acid but the problem with this method is the low yield resulting from cleavage of the glycoside bonds present in the oligosaccharide. For such reasons, the development of a technique to simply and moderately synthesize sugar oxazoline derivatives without using steps such as protection and deprotection is consequently desired in sugar synthesis. However, when we investigate the structure of a sugar oxazoline derivative, we find that there is a dehydration/condensation product between the position 1 hydroxyl group and the amido group of the position 2 deoxy site of the reducing end of the sugar. In other words, if a dehydration/condensation reaction were possible within the molecule, it would be possible to synthesize an oxazoline derivative in one step. If a dehydrating agent is used as an activator of the carbonyl carbon of a carboxylic acid, an oxazoline derivative would be produced if the anomer carbon of the reducing end of a sugar were similarly activated and the anomer carbon were nucleophilically attacked by the carbonyl oxygen of the amido group.

From this viewpoint, the inventors' group proposed methods that employ a water-soluble carbodiimide and a triazine derivative as a dehydrating agent, as mentioned above, but a method of synthesizing the target oxazoline derivative at a high yield by a simple procedure that can be carried out appropriately in an aqueous medium and can be applied to longer sugar chains is still desired.

Means to Solve the Problems

The present inventors have conducted an extensive research and investigation in order to develop the synthesis of sugar oxazoline derivatives useful as sugar donors. As a result, the present inventors have succeeded in discovering that sugar oxazoline derivatives can be synthesized directly from unprotected sugars as the starting materials with haloformamidinium derivatives as the dehydrating agents. The present inventors have also succeeded in producing glycoside compounds in a simple manner with using such oxazoline derivatives as sugar donors. Based on these findings, the present inventors have accomplished the present invention.

In an aspect, the present invention provides the following:

(1) A process for producing an oxazoline derivative of the general formula (3):

[Chemical Formula 3]

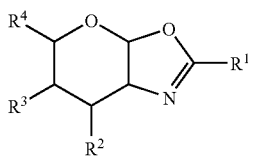

(3)

wherein $R^1$ is an alkyl group, $R^2$, $R^3$, and $R^4$, which may be identical or different one another, are each independently selected from the group consisting of a hydrogen atom, a hydroxyl group, a hydroxymethyl group, an acetamido group, a carboxy group, a sulfuric acid residue, a phosphoric acid residue, a sugar residue and modified derivative residues thereof, which comprises treating a sugar, having a hemiacetalic hydroxyl group and an amido group, of the general formula (1):

[Chemical Formula 1]

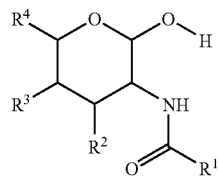

(1)

wherein $R^1$, $R^2$, $R^3$, and $R^4$ have the same meanings as defined above, with a haloformamidinium derivative of the general formula (2):

[Chemical Formula 2]

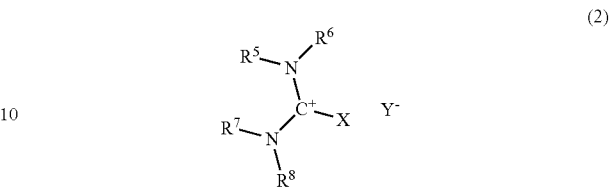

(2)

wherein $R^5$, $R^6$, $R^7$, and $R^8$, which may be identical or different one another, are each independently selected from the group consisting of an unsubstituted or optionally substituted alkyl group, an unsubstituted or optionally substituted alkenyl group, and an unsubstituted or optionally substituted aryl group; $R^5$ taken together with $R^7$, or $R^6$ taken together with $R^8$, may form a ring; or $R^5$ taken together with $R^6$, or $R^7$ taken together with $R^8$, may form a ring; X is a halogen atom; and $Y^-$ is an anion.

(2) The process according to the above (1) wherein Y is a halogen atom, OH, $BF_4$, or $PF_6$, and the sugar of the general formula (1) is reacted with the haloformamidinium derivative of the general formula (2) in an aqueous solvent.

(3) The process according to the above (1) or (2) wherein
(i) the sugar of the general formula (1) is selected from the group consisting of N-acetylglucosamine, N-acetylgalactosamine, and N-acetylmannosamine,
(ii) the sugar of the general formula (1) is selected from the group consisting of N-acetyllactosamine, N,N'-diacetylchitobiose, hyaluronic acid disaccharide, and glycosaminoglycan disaccharide, or
(iii) the sugar of the general formula (1) is selected from the group consisting of N-linked glycoprotein saccharides, O-linked glycoprotein saccharides, and chitooligosaccharides.

(4) A process for producing a glycoside compound which comprises treating a sugar, having a hemiacetalic hydroxyl group and an amido group, of the general formula (1) wherein $R^1$, $R^2$, $R^3$, and $R^4$ have the same meanings as defined above, with a haloformamidinium derivative of the general formula (2) wherein $R^5$, $R^6$, $R^7$, $R^8$, X, and $Y^-$ have the same meanings as defined above, to form an oxazoline derivative of the general formula (3) wherein $R^1$, $R^2$, $R^3$, and $R^4$ have the same meanings as defined above, and then contacting the resulting oxazoline derivative of the general formula (3), used as a sugar donor, with glycosyltransferase or glycoside hydrolase in the presence of a sugar acceptor to form a sugar chain-added compound.

(5) The process according to the above (4) wherein the glycosyltransferase or glycoside hydrolase is selected from the group consisting of chitinase, mutant chitinase, endo-β-N-acetylglucosaminidase M, endo-β-N-acetylglucosaminidase A, hyaluronidase, and chondroitinase.

(6) The process according to the above (4) or (5) wherein
(i) the sugar of the general formula (1) is selected from the group consisting of N-acetylglucosamine, N-acetylgalactosamine, and N-acetylmannosamine,
(ii) the sugar of the general formula (1) is selected from the group consisting of N-acetyllactosamine, N,N'-diacetylchitobiose, hyaluronic acid disaccharide, and glycosaminoglycan disaccharide, or
(iii) the sugar of the general formula (1) is selected from the group consisting of N-linked glycoprotein saccharides, O-linked glycoprotein saccharides, and chitooligosaccharides.

(7) An oxazoline derivative of the general formula (4):

[Chemical Formula 4]

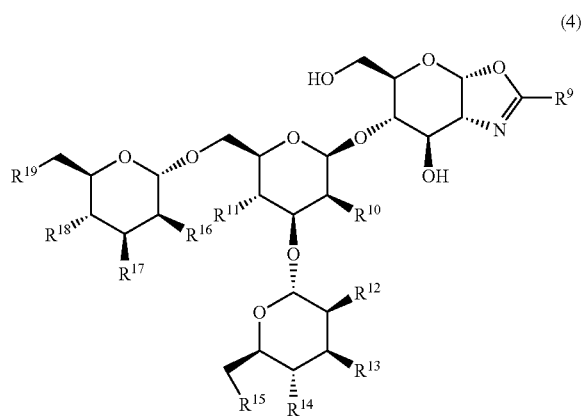

(4)

wherein $R^9$ is an alkyl group, $R^{10}$ to $R^{19}$, which may be identical or different one another, are each independently selected from the group consisting of a hydrogen atom, a hydroxyl group, an acetamido group, a carboxy group, a sulfuric acid residue, a phosphoric acid residue, a sugar residue and modified derivative residues thereof, provided that at least one of $R^{10}$ to $R^{19}$ is a sugar residue.

(8) A process for producing a glycoside compound which comprises contacting an oxazoline derivative of the general formula (4) wherein $R^9$ to $R^{19}$ have the same meanings as defined above, serving as a sugar donor, with glycosyltransferase or glycoside hydrolase in the presence of a sugar acceptor to form a sugar chain-added compound.

Advantageous Effects of the Invention

The present invention provides simple, moderate and single-step productive techniques for the synthesis of oxazoline derivatives serving as sugar donors from unprotected sugars even in good yields. The inventive techniques can be applied to longer sugar chains, and can achieve the glycosylation of various sugars (oligosaccharides and polysaccharides, including branched sugars) onto various compounds and sugars. It is therefore useful in the production of substances for various applications in connection with, for example, bioactive oligosaccharides, carriers for drug delivery systems, surfactants, glycopharmaceuticals, glycopeptides, glycoproteins, glycopolymers, and the like.

The above objects and other objects, features, advantages, and aspects of the present invention are readily apparent to those skilled in the art from the following disclosures. It should be understood, however, that the disclosures in the specification including the following best modes of carrying out the invention, examples, and others are illustrating preferred embodiments of the present invention and given for purposes of illustration only. It will become readily apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BEST MODE FOR CARRYING OUT THE INVENTION

Figure 1:
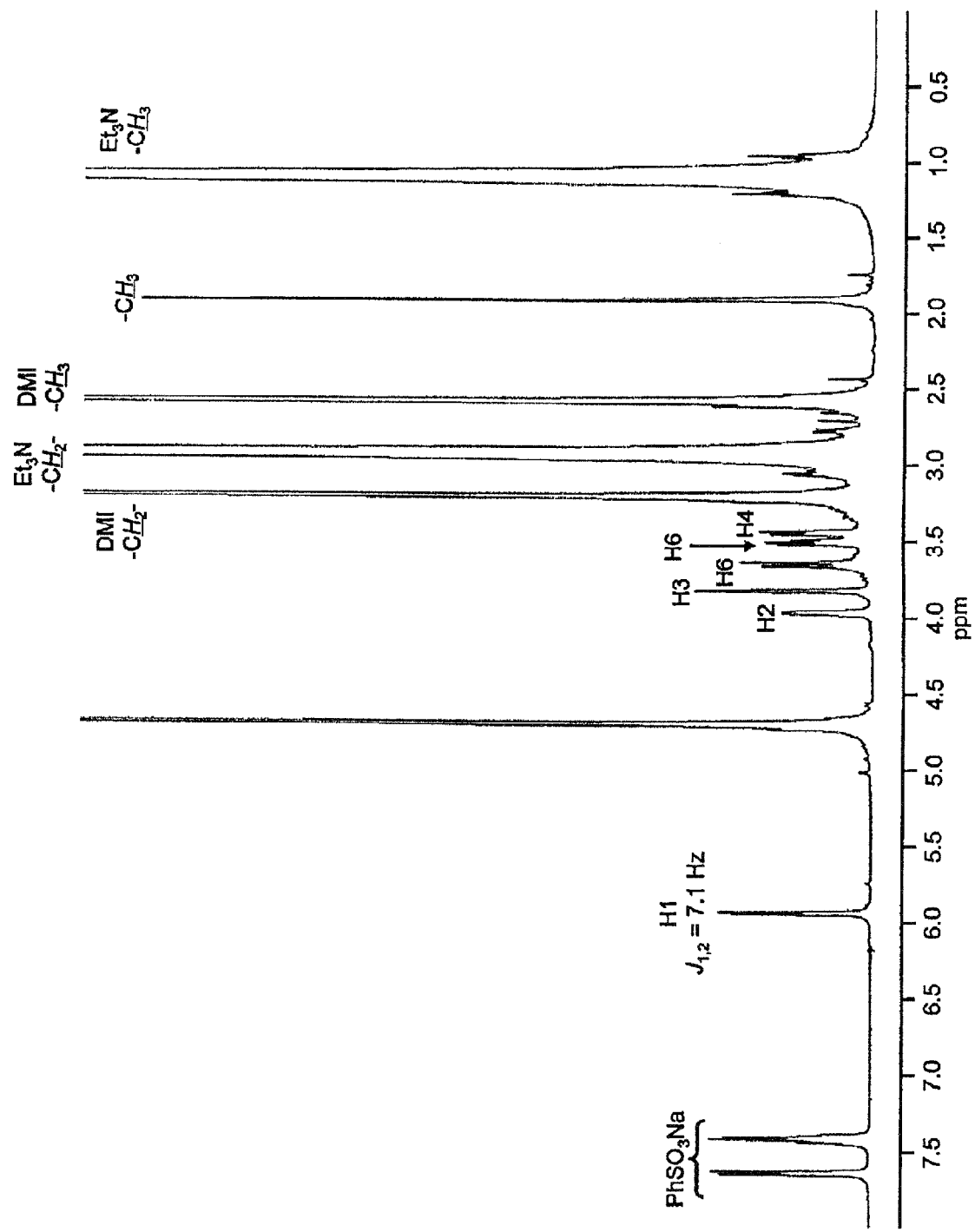
FIG. 1 is the $^1$H-NMR spectrum of the target compound-containing reaction solution obtained in Working Example 1, wherein DMI is 1,3-dimethyl-2-imidazolidinone, $Et_3N$ is triethylamine, and $PhSO_3Na$ is sodium benzenesulfonate.

The present invention provides a process for producing an oxazoline derivative from an unprotected sugar chain as the starting material and a novel compound obtained by said process as well as a process for producing a glycoside compound wherein said oxazoline derivative is used as a sugar donor (or glycosyl donor).

The oxazoline derivative is not particularly limited to, as long as it is derived from a sugar and has the activity to function as a sugar donor. However, one synthesized from a hemiacetalic hydroxyl group- and amido group-bearing sugar, such as an unprotected sugar or an unprotected sugar chain, is preferred. Examples thereof include oxazoline derivatives of the above general formula (3).

The above oxazoline derivative (3) can be produced by treating a hemiacetalic hydroxyl group- and amido group-bearing sugar of the general formula (1) with a haloformamidinium derivative of the general formula (2) that is a dehydrating agent, as illustrated in the following reaction scheme.

[Chemical Formula 5]

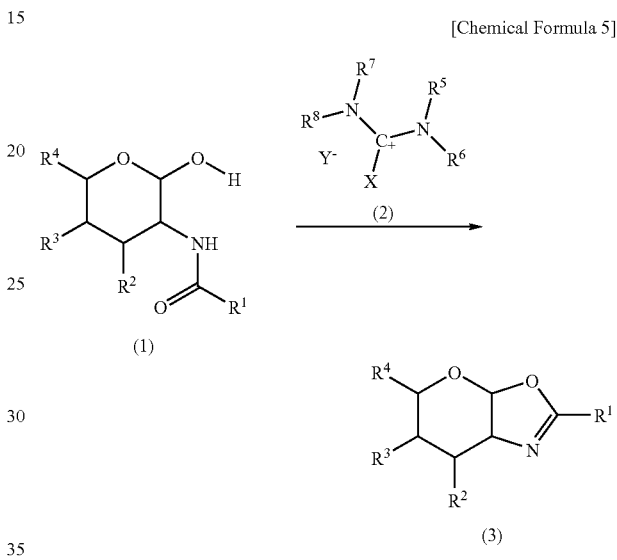

wherein R$^1$ is an alkyl group; R$^2$, R$^3$, and R$^4$, which may be identical or different one another, are each independently selected from the group consisting of a hydrogen atom, a hydroxyl group, a hydroxymethyl group, an acetamido group, a carboxy group, a sulfuric acid residue, a phosphoric acid residue, a sugar residue and modified derivative residues thereof; R$^5$, R$^6$, R$^7$, and R$^8$, which may be identical or different one another, are each independently selected from the group consisting of an unsubstituted or optionally substituted alkyl group, an unsubstituted or optionally substituted alkenyl group, and an unsubstituted or optionally substituted aryl group; R$^5$ taken together with R$^7$, or R$^6$ taken together with R$^8$, may form a ring; or R$^5$ taken together with R$^6$, or R$^7$ taken together with R$^8$, may form a ring; X is a halogen atom; and Y$^-$ is an anion.

The "alkyl group" as used herein may be either linear or branched. Representatives of said alkyl group include C$_{1-22}$ alkyl, such as methyl, ethyl, propyl, isopropyl, butyl, isobutyl, sec-butyl, tert-butyl, pentyl, isopentyl, tert-pentyl, hexyl, heptyl, octyl, nonyl, decanyl, hexadecanyl and eicosanyl; preferably C$_{1-6}$ alkyl, such as methyl, ethyl, propyl, isopropyl, butyl, tert-butyl and pentyl; even more preferably C$_{1-4}$ alkyl, such as methyl, ethyl, propyl, isopropyl, butyl and tert-butyl.

The term sugar residue as used herein may refer to any residue derived from a sugar. The term "sugar" used herein may be interpreted to mean that it includes sugars, carbohydrates, saccharides, complex sugars, sugar conjugates and other sugar-related compounds. The term "sugars" may refer to monosaccharides, simple sugars produced by condensation of multiple sugar units (wherein said simple sugar includes disaccharides and oligosaccharides), and polysaccharides. The sugar may refer to polyhydroxyaldehydes or polyhydroxyketones wherein basically the number of oxygen atoms is almost identical with the number of carbon atoms, and their derivatives (for example, amino sugars with an amino group, carboxylic acids in which the aldehyde group or the primary hydroxyl moiety is replaced with a carboxyl group, polyhydric alcohols in which the aldehyde group or the ketone group is replaced with a hydroxyl group, etc.) and polycondensates thereof. The term "carbohydrate" may be interpreted to mean any substance having a sugar as a main component; those substances consisting of only sugar may be considered simple carbohydrates and those that contain other substances (including protein, fat, synthetic polymers, and the like) may be considered complex carbohydrates.

The sugar according to the present invention is not particularly limited to, as to its source or origin and encompasses those obtained from natural origins, those produced by genetically engineered animal cells, plant cells, microorganisms, and other cells, those enzymatically manufactured, those manufactured by fermentation processes, those artificially synthesized by chemical processes and others. The sugar may encompass monosaccharides, disaccharides, oligosaccharides, and polysaccharides. Examples of the monosaccharide include glucose, galactose, mannose, glucosamine, N-acetylglucosamine, galactosamine, N-acetylgalactosamine, mannosamine, N-acetylmannosamine, fructose, glucuronic acid, iduronic acid, etc. Examples of the disaccharide include maltose, isomaltose, lactose, lactosamine, N-acetyllactosamine, cellobiose, melibiose, N,N'-diacetylchitobiose, hyaluronic acid disaccharide, glycosaminoglycan disaccharide, etc. The term oligosaccharide encompasses those molecules composed of two or more monosaccharide units bound together in the ordinary sense, usually those composed of 2 to 30 monosaccharide units, and typically those composed of 2 to 20 monosaccharide units. Examples of the oligosaccharide include homooligomers composed of glucose, galactose, mannose, glucosamine, N-acetylglucosamine, fructose, and others; heterooligomers composed of two or more different units selected from glucose, galactose, mannose, glucosamine, N-acetylglucosamine, fructose, sialic acid, and others. Representatives of the oligosaccharide include maltooligosaccharide, isomaltooligosaccharide, lactooligosaccharide, lactosamine oligosaccharide, N-acetyllactosamine oligosaccharide, cellooligosaccharide, melibiooligosaccharide, N-acetylchitotriose, N-acetylchitotetraose, N-acetylchitopentose, etc. Other examples thereof include, for example, glycosaminoglycan oligosaccharides, hyaluronic acid oligosaccharide (for example, hyaluronic acid disaccharide as aforementioned, and hyaluronic acid tetrasaccharide, and the like), chondroitin sulfate oligosaccharides (for example, chondroitin sulfate A oligosaccharide, chondroitin sulfate C oligosaccharide, and the like), keratan sulfate oligosaccharides, heparin oligosaccharides, heparan sulfate oligosaccharides, and the like. Examples of the polysaccharide include those discovered in a wide range of organisms such as animals, plants (including seaweeds), insects, microorganisms, and others. Representatives of the polysaccharide include sialo complex-type sugars, N-linked sugar chains, O-linked sugar chains, glycosaminoglycan, starch, amylose, amylopectin, cellulose, chitin, glycogen, agarose, alginic acid, hyaluronic acid, inulin, glucomannan, etc.

Typical examples of the sugar residue and modified derivative residue thereof include those remainders formed at position 1 of a monosaccharide or at position 1 on the reducing end of an oligosaccharide. The term "modified sugar" (or "modified derivative thereof") used herein may refer to those modified through any process of isolation, separation and purification from naturally-occurring sources and origins, those that have been enzymatically modified, those that have been chemically modified, those that have been modified by biochemical means, including microorganisms, wherein such modifications may comprises those known in the field of glycoscience, for example, hydrolysis, oxidation, reduction, esterification, acylation, amination, etherification, nitration, dehydration, glycosylation, etc.

The applicable hemiacetalic hydroxyl- and amido-bearing sugar used as the starting material in implementing the present invention usually includes sugar molecules having an amido group at position 2 on the reducing end side; preferably sugars having an acetamido group at position 2 on the reducing end side, including, for example, N-acetylglucosamine, N-acetylgalactosamine, N-acetylmannosamine, etc. in case of monosaccharides; and sugars in which the reducing end is selected from N-acetylglucosamine, N-acetylgalactosamine, and the like, in case of disaccharides, oligosaccharides, and polysaccharides. Suitable examples of the starting material sugar include N-acetylglucosamine, N-acetylgalactosamine, N-acetylmannosamine, and the like, N-acetyllactosamine, N,N'-diacetylchitobiose, hyaluronic acid disaccharide, glycosaminoglycan disaccharide, and the like, and N-linked glycoprotein saccharides, O-linked glycoprotein saccharides, chitooligosaccharide, and the like.

Herein, examples of the "alkyl group" in the "unsubstituted or optionally substituted alkyl group" are the same as aforementioned. The "alkenyl group" in the "unsubstituted or optionally substituted alkenyl group" may be linear or branched, and include, for example, a $C_{2-24}$ alkenyl group (for example, vinyl, allyl, isopropenyl, 1-butenyl, 2-butenyl, 3-butenyl, 2-methyl-2-propenyl, 1-methyl-2-propenyl, 2-methyl-1-propenyl, and the like). Examples of the "aryl group" in the "unsubstituted or optionally substituted aryl group" include, for example, $C_{6-14}$ aryl (for example, phenyl, 1-naphthyl, 2-naphthyl, 2-biphenylyl, 3-biphenylyl, 4-biphenylyl, 2-anthryl, 3-indenyl, 5-fluorenyl, and the like). A phenyl group is preferred.

The "alkyl group", "alkenyl group", and "aryl group" in the "unsubstituted or optionally substituted alkyl group", "unsubstituted or optionally substituted alkenyl group", and "unsubstituted or optionally substituted aryl group" may be substituted optionally with one or more substituents. When substituted, the "substituent" may be any substituent known in the field, for example, oxo, thioxo, unsubstituted or optionally substituted imino, halogen (e.g., fluorine, chlorine, bromine, iodine), $C_{1-3}$ alkylenedioxy (e.g., methylenedioxy, ethylenedioxy, and the like), nitro, cyano, $C_{1-6}$ alkyl, $C_{2-6}$ alkenyl, carboxy $C_{2-6}$ alkenyl (e.g., 2-carboxyethenyl, 2-carboxy-2-methylethenyl, and the like), $C_{2-6}$ alkynyl, $C_{3-6}$ cycloalkyl, $C_{6-14}$ aryl (e.g., phenyl, 1-naphthyl, 4-biphenylyl, 2-anthryl, and the like), $C_{1-8}$ alkoxy, $C_{1-6}$ alkoxy-carbonyl-$C_{1-6}$ alkoxy (e.g., ethoxycarbonylmethyloxy, and the like), hydroxy, $C_{6-14}$ aryloxy (e.g., phenyloxy, and the like), $C_{7-16}$ aralkyloxy (for example, benzyloxy, and the like), mercapto, alkylthio, $C_{6-14}$ arylthio (e.g., phenylthio, and the like), $C_{7-16}$ aralkylthio (for example, benzylthio, and the like), amino, mono-$C_{1-6}$ alkylamino (e.g., methylamino, ethylamino, and the like), mono-$C_{6-14}$ arylamino (e.g., phenylamino, and the like), di-$C_{1-6}$ alkylamino (e.g., dimethylamino, diethylamino, and the like), di-$C_{6-14}$ arylamino (e.g., diphenylamino, and the like), formyl, carboxy, $C_{1-6}$ alkyl-carbonyl (e.g., acetyl, propionyl, and the like), $C_{3-6}$ cycloalkyl-carbonyl (e.g., cyclopropylcarbonyl, and the like), $C_{1-6}$ alkoxy-carbonyl (e.g., methoxycarbonyl, ethoxycarbonyl, propoxycarbonyl, tert-butoxycarbonyl, and the like), $C_{6-14}$ aryl-carbonyl (e.g., benzoyl, and the like), $C_{7-16}$ aralkyl-carbonyl (e.g., phenylacetyl, and the like), $C_{6-14}$ aryloxy-carbonyl (e.g., phenoxycarbonyl, and the like), $C_{7-16}$ aralkyloxy-carbonyl (e.g., benzyloxycarbonyl, and the like), 5- or 6-membered heterocycle carbonyl (e.g., nicotinoyl, tenoyl, furoyl, morpholinocarbonyl, thiomorpholinocarbonyl, piperazin-1-ylcarbonyl, pyrrolidin-1-ylcarbonyl, and the like), carbamoyl, thiocarbamoyl, mono-$C_{1-6}$ alkyl-carbamoyl (e.g., methylcarbamoyl, and the like), di-$C_{1-6}$ alkyl-carbamoyl (e.g., dimethylcarbamoyl, and the like), $C_{6-14}$ aryl-carbamoyl (e.g., phenylcarbamoyl, and the like), 5- or 6-membered heterocycle carbamoyl (e.g., 3-pyridylcarbamoyl, 2-thienylcarbamoyl, and the like), $C_{1-6}$ alkylsulfonyl (e.g., methylsulfonyl, and the like), $C_{6-14}$ arylsulfonyl (e.g., phenylsulfonyl, and the like), $C_{1-6}$ alkylsulfinyl (e.g., methylsulfinyl, and the like), $C_{6-14}$ arylsulfinyl (e.g., phenylsulfinyl, and the like), formylamino, $C_{1-6}$ alkyl-carbonylamino (e.g., acetylamino, and the like), $C_{6-14}$ aryl-carbonylamino (e.g., benzoylamino, and the like), $C_{1-6}$ alkoxycarbonylamino (e.g., methoxycarbonylamino, and the like), $C_{1-6}$ alkylsulfonylamino (e.g., methylsulfonylamino, and the like), $C_{6-14}$ arylsulfonylamino (e.g., phenylsulfonylamino, and the like), $C_{1-6}$ alkyl-carbonyloxy (e.g., acetoxy, and the like), $C_{6-14}$ aryl-carbonyloxy (e.g., benzoyloxy, and the like), $C_{1-6}$ alkoxy-carbonyloxy (e.g., methoxycarbonyloxy, and the like), mono-$C_{1-6}$ alkyl-carbamoyloxy (e.g., methylcarbamoyloxy, and the like), di-$C_{1-6}$ alkyl-carbamoyloxy (e.g., dimethylcarbamoyloxy, and the like), $C_{6-14}$ aryl-carbamoyloxy (e.g., phenylcarbamoyloxy, and the like), nicotinoyloxy, unsubstituted or optionally substituted 5- to 7-membered saturated ring amino, 5- to 10-membered aromatic heterocyclic group (e.g., 2-thienyl, 2-pyridyl, 3-pyridyl, 4-pyridyl, 2-quinolyl, 4-quinolyl, 8-quinolyl, 4-isoquinolyl, 1-indolyl, 3-indolyl, 2-benzothiazolyl, 2-benzo[b]thienyl, 2-benzo[b]furanyl, 3-benzo[b]furanyl, and the like), sulfo, sulfamoyl, sulfinamoyl, sulfenamoyl, and the like. The "alkyl moiety" (including the alkyl moiety in an alkoxy group), "alkylene moiety", "alkenyl moiety", "alkynyl moiety" "aryl moiety", and "heterocycle moiety" in the substituents given here as examples may be optionally substituted by one or more substituents, and the substituents in this case may be as explained above. The substituents when "optionally substituted" in the above explanation of "substituents" may similarly be substituents as explained above.

When "$R^5$ taken together with $R^7$, or $R^6$ taken together with $R^8$, form a ring", the "ring" may be a 5- to 7-membered ring formed from a carbon chain taken together with the nitrogen atoms bound to $R^5$ and $R^7$ or the nitrogen atoms bound to bond $R^6$ and $R^8$, that may also contain optionally one or more oxygen atoms, nitrogen atoms and/or sulfur atoms. The ring may include, for example, an imidazoline ring, a benzimidazoline ring, a hydropyrimidine ring, or the like. When "$R^5$ taken together with $R^6$, or $R^7$ taken together with $R^8$, form a ring", the "ring" may be a 5- to 7-membered ring formed from a carbon chain taken together with the nitrogen atoms bound to $R^5$ and $R^6$ or the nitrogen atoms bound to $R^7$ and $R^8$, that may also contain optionally one or more oxygen atoms nitrogen atoms and/or sulfur atoms, including, for example, a pyrrolidine ring, a piperidine ring, a piperazine ring, a morpholine ring, a thiomorpholine ring, or the like. X is halogen; e.g., chlorine, bromine, iodine, etc.

$Y^-$ is not particularly limited to, as long as it is an anion. Suitable examples of Y include halogen such as chlorine, bromine, and iodine, OH, $BF_4$, $PF_6$, and others.

The haloformamidinium derivative (2) can be obtained by treating the corresponding urea derivative with a suitable halogenating agent, such as a chlorinating agent. Examples of the halogenating agent include phosgene, oxazolyl chloride, phosphorus pentachloride, phosphorus trichloride, phosphorus oxychloride, their corresponding bromides, and the like. Specific examples of the compound (2) include 2-chloro-1,3-dimethylimidazolinium chloride (DMC),

[Chemical Formula 6]

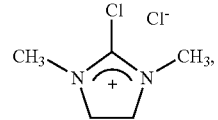

2-chloro-1,3-dimethylimidazolinium hexafluorophosphate, N,N,N',N'-tetramethylchloroformamidinium chloride, chloro-N,N,N',N'-bis(tetramethylene)formamidinium hexafluorophosphate, 2-chloro-1,3-dimethyl-3,4,5,6-tetrahydro-2(1H)-pyrimidinium chloride, and the like.

The synthesis reaction of the compound (3) using the compound (2) can be carried out in a medium such as a solvent known in the field as long as it does not adversely affect the reaction. It is advantageous to conduct this reaction without a solvent (including cases where the starting materials may also serve as solvents) or in the present of a solvent inert in the reaction. This solvent is not particularly limited to, as long as the reaction progresses, but aqueous solvents are preferred. Examples of such solvents include water; alcohols, such as methanol, ethanol, n-propanol, isopropanol, cyclohexanol, furfuryl alcohol, ethylene glycol and benzyl alcohol; ethers, such as tetrahydrofuran (THF), dioxane, tetrahydrofurfuryl alcohol, diethylene glycol, cyclohexyl methyl ether, methyl cellosolve, cellosolve, butyl cellosolve and methyl tert-butanol; ketones, such as methyl ethyl ketone, furfural, methyl isobutyl ketone, methyl oxide, diacetone alcohol and cyclohexanone; nitriles, such as acetonitrile and benzonitrile; sulfoxides, such as dimethyl sulfoxide (DMSO) and sulfolane; amides, such as formamide, N,N-dimethylformamide (DMF) and N,N-dimethylacetamide; esters, such as methyl formate, ethyl formate, ethyl acetate, butyl acetate, methoxybutyl acetate, cellosolve acetate, diethyl carbonate and glycol carbonate; organic acids, such as formic acid, acetic acid, propionic acid and acetic anhydride; heterocyclic compounds, such as hexamethylphosphorotriamide, pyridine and quinoline; aromatic amines, such as aniline and N-methylaniline; nitro compounds, etc. These solvents can be used alone, or in the mixture of two or more species thereof at appropriate proportions, for example, at 1:1 to 1:1000, as needed.

The reaction medium utilizable in this reaction is water and any of organic solvents conventionally used in the art, but water or an aqueous organic solvent is preferred, and an amine-containing salt solution is even more preferred. An aqueous salt solution with a buffering capacity can also be used. The buffer can be selected from among those known in the field as long as it does not adversely affect the reaction.

In a typical case, the hydrogen ion concentration pH of the amine solution is ranging from 1.0 to 13, more preferably from 7.5 to 11. The reaction temperature is ranging preferably from −80° C. to 80° C., even more preferably ranging from 0 to 40° C. The reaction time is not particularly limited to, but can be selected from appropriate periods as long as the desired product is obtained. For example, it may be from one minute to 24 hours, usually from 15 minutes to 5 hours, and typically from 15 minutes to 2 hours. The amount of dehydrating agents is not particularly limited to, but it is preferable to use 1 to 5 Eq versus the sugar used. The amine concentration is 0.1 to 100 Eq, preferably 1 to 4 Eq, versus the dehydrating agent used. The concentration of the sugar added is preferably 0.1 mM to 5 M, more preferably 10 mM to 1 M.

The amine may be a primary amine, a secondary amine, a tertiary amine, or a quaternary amine. Examples of the amine include those having an aliphatic hydrocarbon residue, an aromatic hydrocarbon residue, a heterocyclic residue, and the like. The aliphatic hydrocarbon residue may be linear or branched, saturated or unsaturated, and includes, for example, alkyl, alkenyl, cycloalkyl, aralkyl, cycloalkylalkyl, and the like. The aromatic hydrocarbon residue may be monocyclic or condensed multicyclic wherein two or more rings are fused. Examples of the aromatic hydrocarbon residue include phenyl, naphthyl, and the like. The heterocyclic residue may have one or more hetero atoms selected from the group consisting of sulfur, oxygen, and nitrogen, and encompasses pyridyl, imidazolyl, thiazolyl, quinolinyl, and the like. This amine also encompasses piperidine, morpholine, thiomorpholine, piperazine, pyrrolidine, and the like. Representatives of the amine include tertiary amines and diamines, having an aliphatic hydrocarbon residue, such as trimethylamine, triethylamine, diethylmethylamine, dimethylethylamine, n-butyldimethylamine, diisopropylethylamine and tetramethylethylenediamine.

The product can be used in the form of the reaction solution or as a crude product in the following reaction, but it can also be isolated from the reaction mixture by the following ordinary methods. It can be isolated, separated and purified by concentration, vacuum concentration, distillation, fractional distillation, solvent extraction, liquid conversion, re-extraction (transfer among solvents), chromatography, such as high-performance liquid chromatography (HPLC), thin-layer chromatography (TLC) and column chromatography, crystallization, recrystallization, and other isolation, separation and purification techniques.

Among the oxazoline derivatives (3) obtained according to the present invention, the oxazoline derivatives of the general formula (4) wherein $R^9$ is an alkyl group, $R^{10}$ to $R^{19}$, which may be identical or different each other, are each independently selected from the group consisting of hydrogen, hydroxyl, acetamido, carboxy, a sulfuric acid residue, a phosphoric acid residue, a sugar residue and modified derivative residues thereof; provided that at least one of $R^{10}$ to $R^{19}$ is a sugar residue, are novel and are useful as sugar donors (glycosyl donors). Here, the substituents $R^9$ to $R^{19}$ are the same groups as aforementioned in connection with $R^1$ to $R^4$. This oxazoline derivative (4) is useful as a sugar donor for the synthesis of sugar chain-added compounds (or saccharide chain-linked compounds) and oligosaccharide compounds. For example, they are useful when used for various applications such as to synthesize bioactive oligosaccharides, carriers for drug delivery systems, surfactants, glycopharmaceuticals (carbohydrate-based drugs), glycopeptides, glycoproteins, glycopolymers, and other useful substances. Representatives of the oxazoline derivative (4) include those compounds wherein $R^9$ is alkyl and $R^{10}$ to $R^{19}$, which may be identical or different each other, are each independently selected from the group consisting of hydroxyl, acetamido, a sugar residue and modified derivative residues thereof; provided that at least one of $R^{10}$ to $R^{19}$ is a sugar residue.

The oxazoline derivative (3) obtained in accordance with the present invention can be used as a sugar donor and subjected to transglycosylation in the presence of a sugar acceptor to afford an organic compound wherein a sugar chain is incorporated, that is, a glycoside compound. Methods that employ an enzyme are preferably applicable to this transglycosylation. The enzyme is not particularly limited to, as long as it is capable of carrying out the required reaction. The enzyme as can be utilized herein is, for example, selected from those known as enzymes that catalyze the transfer of glycosyl groups from one compound to another. These enzymes can be used alone, or in the mixture of two or more species at suitable ratios as needed. The transglycosylation-catalyzing enzyme used in transglycosylation is not particularly limited to, but representatives of said enzyme are glycosyltransferase and glycohydrolase (or glycoside hydrolase). The oxazoline derivative (3) preferably gives a glycoside compound with use of glycohydrolase.

The glycohydrolase encompasses those obtained from animals, including human beings, plants, and microorganisms, recombinant enzymes produced by genetic engineering, mutant enzymes, immobilized enzymes, and the like. Representatives of said glycohydrolases include chitinase, mutant chitinase, endoglycosidases such as endo-β-N-acetylglucosaminidase, hyaluronidase, chondroitinase, and the like. The chitinase and mutant chitinase encompass chitinases derived from organisms of the genus *Bacillus*. Examples of said enzymes are disclosed by S. Shoda et al. in *Helvetica Chemic Acta*, Vol. 85, pp. 3919-3936 (2002), and include, for example, chitinase A1 derived from *Bacillus* circulars WL-12 and mutant chitinases, specifically, E204Q, D202N, D200N, Y279F, D280N, W433F, and the like. Typical examples of the endoglycosidases are endo-β-N-acetylglucosaminidases, and include, for example, endo-β-N-acetylglucosaminidase M (Endo M) derived from *Mucor hiemalis* (Yamamoto, K. et al., *Biochem. Biophys. Res. Commun.*, 203, pp. 244-252 (1994)), endo-β-N-acetylglucosaminidase A (Endo A) derived from *Arthrobacter protophormiae* (Takegawa, K. et al., *Biochem. Int.*, 24, pp. 849-855 (1991)), and the like. Examples of the hyaluronidases include those derived from mammals such as testes, seminal fluid, skin, and spleen of higher animals, those obtained from leeches, bee venom, snake venom, and those obtained from microorganisms such as *Pneumococcus*, *Streptococcus*, *Staphylococcus*, *Clostridium*, and the like. Representatives of the hyaluronidases are bovine testicular hyaluronidase, ovine testicular hyaluronidase, and the like. The chondroitinases include, for example, those derived from *Flavobacterium heparinum*, those derived from *Proteus vulgaris* those derived from *Arthrobacter aurescens*, and the like. Chondroitinase ABC (*Proteus vulgaris*), chondroitinase ACII Arthro (*Arthrobacter aurescens*), chondroitinase B (*Flavobacterium heparinum*) (Seikagaku Corp.), and the like are available commercially.

The enzyme may be used without any modification or optionally in an immobilized form. Immobilization can be carried out by techniques well known to those in the art (for example, cross-linking, physical adsorption, encapsulation, etc.). The utilizable immobilization carrier may be any conventionally used carrier, and includes, for example, polysaccharides such as cellulose, agarose, dextran, κ-carrageenan, alginic acid, gelatin and cellulose acetate; natural polymers such as gluten; inorganic materials such as activated charcoal, glass, clay, kaolinite, alumina, silica gel, bentonite, hydroxyapatite and calcium phosphate; synthetic polymers such as polyacrylamide, polyvinyl alcohol, polypropylene glycol and urethane; and others. The carrier may also encompass cross-linked carriers, those having a bonded ion-exchange group such as a diethylaminoethyl group and a carboxymethyl group, and those that have been pre-activated by activating techniques such as BrCN treatment, epoxidation, and N-hydroxysuccinimidation, and others. The carrier as can be utilized herein is selected from commercially-available products for applications of enzyme immobilization and ligand immobilization. Microorganisms that produce such enzymes can also be used herein. The microorganism cells in such cases can be used in a microencapsulated form, in the form of immobilized cells, or can be applied to a suitable method selected from those known in the field.

The process of the glycosylation reaction according to the present invention is not particularly limited to, as long as it is capable of subjecting the above sugar donor oxazoline derivative (3) to the action of a transglycosylation reaction-catalyzing enzyme such as glycohydrolase in the presence of a sugar acceptor (or glycosyl acceptor) to form a glycoside compound. The reaction is initiated by mixing an enzyme-containing buffer or aqueous solution with an aqueous starting material compound solution. The reaction can usually be carried out in water, in a mixed system composed of water and a water-miscible organic solvent, or in a two-phase liquid system composed of a substantially water-insoluble or poorly water-soluble organic solvent and water. However, an aqueous system is generally preferred. If necessary, the starting material can also be used after dissolving it in a suitable organic solvent, such as ethanol, methanol, dioxane and dimethylsulfoxide, and then converting the resulting solution into an aqueous solution. The reaction conditions can be selected within ranges wherein they do not adversely affect the production of the glycosylated product. The concentration of the substrates, sugar donors and sugar acceptors, is ranging from preferably 0.001 to 20%, more preferably 0.01 to 10%. The pH of the reaction solution is ranging from preferably 5 to 13, more preferably 6 to 10. The reaction temperature is ranging from preferably 10 to 50° C., more preferably 20 to 40° C. A buffer (for example, phosphate buffer, citrate buffer, Tris buffer, and the like) can also be used to stabilize the pH. The pH can also be adjusted by using an acid or a base. The reaction time is ranging from 1 minute to 200 hours, preferably 20 minutes to 150 hours, but can be suitably determined depending on each enzyme concentration as well as each sugar donor and sugar acceptor used.

When an enzyme-producing organism (for example, a transformant and the like) is used, sugars such as glucose, organic acids such as acetic acid, and energy sources such as ethanol and glycerol, can be added to make the reaction progress more efficiently. Each of these may be added alone, or in the form of a mixture. The amount of such supplements added is ranging from preferably $\frac{1}{100}$ to 10 fold per substrate. Sugars such as glucose, organic acids such as acetic acid, energy sources including, for example, glycerol and the like, coenzymes, coenzyme-regenerating enzymes, and coenzyme-regenerating enzyme substrates may be used in combination with each other. Although these inherently accumulate in the cells, the addition of these substances as needed herein can sometimes raise the reaction rate, yield, and the like. Suitable substances can be selected appropriately. As needed, the reaction system can contain one or more members selected from the group consisting of substrates, the enzymes of interest, enzyme-producing microorganism cells, cultures thereof, processed products thereof, extracts thereof and others due to sequential or continuous addition thereof. The reaction rate can also be facilitated by conducting the reaction while removing the product continuously.

The reaction can be carried out in a batch process or in a continuous process, and also with use of a membrane reactor and the like. The glycoside compounds produced according to the reaction can be isolated, separated and purified by conventional means for isolation, separation and purification. For example, the reaction solution can be subjected to a usual refining method such as membrane separation, extraction with an organic solvent (for example, toluene, chloroform, and the like), concentration, vacuum concentration, distillation, fractional distillation, crystallization, recrystallization, high-performance liquid chromatography (HPLC), thin-layer chromatography (TLC), column chromatography and the like, directly or after separating the cells when cells have been used. For example, the products can be extracted from the reaction solution with an organic solvent such as butyl acetate, ethyl acetate, toluene, chloroform, or the like after the reaction has been completed, and crude products can be obtained by distilling off the solvent. These crude products may be used directly, or may be refined as needed by separation means such as silica gel column chromatography, followed by purification means including, for example, high-performance liquid chromatography with a carrier such as a cellulose derivative (including an optically active carrier). The target enzymatic reaction can be conducted by bringing the enzyme into contact with the reaction solution, but the contact state between the enzyme and the reaction solution is not limited to these specific examples. The reaction solution is one obtained by dissolving the substrate and the components necessary for the enzymatic reaction in a suitable solvent to create an environment conducive to the expression of the enzymatic activity.

In the glycosylation reaction, glycosylation can be effected by bringing an enzyme into contact with a substrate solution that contains a sugar donor and a sugar acceptor in a batch or continuous system fashion, and methods suited to industrial implementation can be suitably selected. The suitable concentration of the substrate that contains the sugar acceptor and the sugar donor is ranging from approximately 1 to 50 w/v %. In a more preferred embodiment, the concentration of the oxazoline derivative (3) is ranging from approximately 5 to 20 w/v %, and the concentration of the sugar acceptor is from approximately 0.001 to 0.4 mol/L. A metal salt that is useful for stabilizing the enzyme and the like can also be added to the substrate solution.

The selected conditions for the above glycosylation reaction are those under which the enzyme is stable and can act adequately, for example, at a pH of approximately 3 to 10, more preferably a pH of approximately 5 to 10, and a temperature of approximately 20 to 80° C., more preferably approximately 30 to 70° C. For chitinase A1, mutant chitinase, Endo A, Endo M, and the like, pH at which the enzyme is stable can be applicable and the selected pH is, for example, from approximately 4 to 7, preferably from 5.5 to 6. The temperature may be, for example, 50° C. or lower, preferably near 37° C. to permit glycosylation.

According to a preferred practical embodiment of the present invention, a bioreactor comprises a device allowing the contact of an enzyme-immobilized carrier with a liquid to be reacted. Advantageously, the device is selected from a stirred tank reactor, basket reactor, fluidized-bed reactor, packed-bed reactor, filter reactor, and the like. The ordinary application forms of immobilized enzymes comprise a continuous process with a packed column or a batch process wherein it is easy to recover the immobilized enzyme. Similarly, the bioreactor may also represent a device that is a column or a plurality of columns, advantageously in parallel. In the column(s), the substrate to be treated preferably flows in the direction of gravity. Another favorable practical embodiment of the bioreactor also comprises in addition to the device a tank containing the substrate to be treated, a post-treatment tank in which the outflow from the bioreactor is post-processed, and a tank for the storage of the product.

The practical embodiment of the present invention can also provide a method for subjecting the resulting glycosylated glycoside compound product to isolation, separation, and/or purification with liquid chromatography to afford the desired glucoside-containing glycoside compound. For the liquid chromatography, the desired products can be obtained efficiently in an industrially advantageous manner with an ODS reverse-phase column.

The sugar acceptor used herein includes those known in the field, and suitable species can be appropriately selected and used. The sources and origins of the sugar acceptor are not particularly limited to, but said sugar acceptors may encompass those obtained from natural resources, those synthesized by genetically engineered animal cells, plant cells, microorganisms, and the like, those produced enzymatically, those produced by fermentation, those artificially manufactured by chemical synthesis, and the like. Examples of said sugar acceptor include proteins, peptides, lipids, sugars, saccharides or carbohydrates, organic compounds, natural or synthetic polymer compounds, and other compounds, including glycoproteins, glycopeptides, glycolipids, and the like. The sugar acceptor may be an individual substance or a mixture.

The resulting glycoside compounds, that is, sugar chain-added compounds or oligosaccharides, are useful for various applications, such as bioactive oligosaccharides, carriers for drug delivery systems, surfactants, glycopharmaceuticals (carbohydrate-based drugs), glycopeptides, glycoproteins, glycopolymers, and others. The products glycoside compounds are useful in a variety of researches on cell recognition, immunity, cell differentiation, cell migration, fertilization, maturation, tissue morphogenesis, inflammation, wound healing, cancer metastasis, tumorigenesis, and others.

The techniques according to the present invention can be applied to highly regioselective and/or stereoselective glycosylation. Also, since the technique can also be applied to long sugar chains, the variety of glycosylation can be increased and new oligosaccharides and/or polysaccharides can be introduced into peptides, proteins, lipids, saccharides, carbohydrates, and other compounds. Since the technique of the present invention makes it possible to produce sugar oxazoline derivatives that serve as sugar donors and glycoside compounds, by using oligosaccharides and others, the structure of which is elucidated, it is advantageous for applications in various fields such as pharmaceuticals, agricultural chemicals, cosmetics, and the like. The present invention makes it possible to provide techniques for production of sugar microarrays (sugar chips).

Details of the present invention are described by the following working examples but such working examples are provided only for illustrative purposes, and for referential embodiments of the present invention. These examples have been described herein for the purpose of illustrating specific embodiments of the present invention but should not be construed as in any sense limiting the scope of the invention disclosed herein. It should be understood in the present invention that various embodiments can be made or executed within the spirit, scope and concept disclosed herein. All the examples were carried out or can be carried out, unless otherwise disclosed herein specifically, by standard techniques which are well known and conventional to those skilled in the art.

WORKING EXAMPLE 1

To 83.9 mg (0.496 mmol) of 2-chloro-1,3-dimethylimidazolinium chloride was added 27.7 mg (0.125 mmol) of N-acetylglucosamine, 208 µL (1.50 mmol) of triethylamine, and 500 µL of deuterated water (heavy water) and the resultant mixture was stirred for one hour at room temperature. When this reaction solution was analyzed by NMR it was verified that an N-acetylglucosamine oxazoline derivative of the following formula:

[Chemical Formula 7]

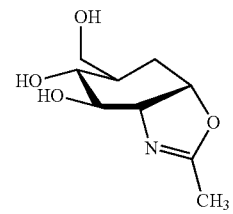

was obtained (yield: 83%).

Figure 2:
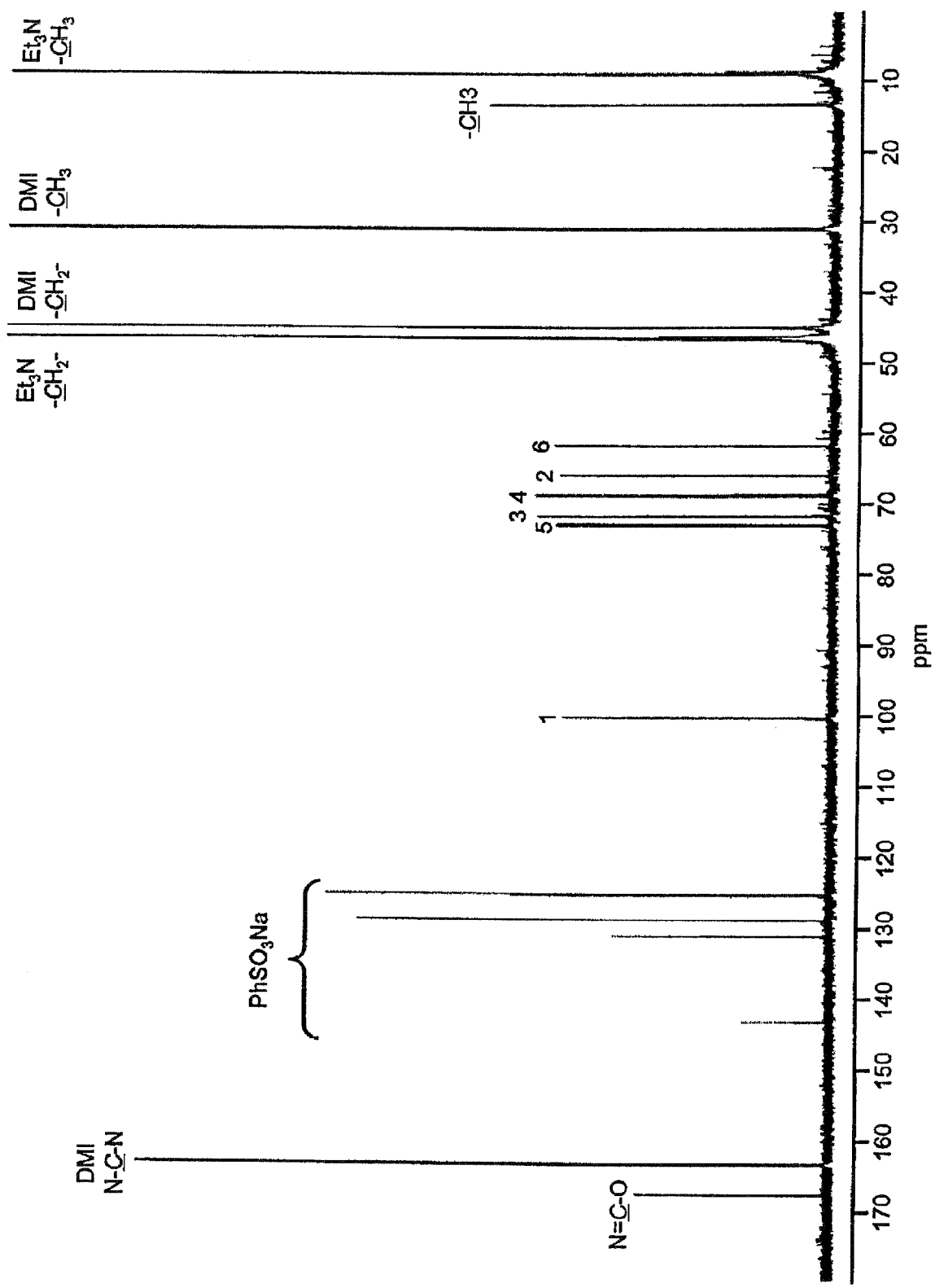
FIG. 2 is the $^{13}$C-NMR spectrum of the target compound-containing reaction solution obtained in Working Example 1, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 1 shows the $^1$H-NMR spectrum and FIG. 2 shows the $^{13}$C-NMR spectrum of the reaction solution containing the target compound.

WORKING EXAMPLE 2

To 41.6 mg (0.246 mmol) of 2-chloro-1,3-dimethylimidazolinium chloride was added 5.5 mg (24.9 µmol) of N-acetylmannosamine, 104 µL (0.750 mmol) of triethylamine, and 500 µL of deuterated water and the resultant mixture was stirred for one hour at room temperature. When this reaction solution was analyzed by NMR, it was verified that an N-acetylmannosamine oxazoline derivative of the following formula:

[Chemical Formula 8]

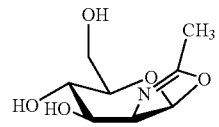

was obtained (yield: 76%).

Figure 3:
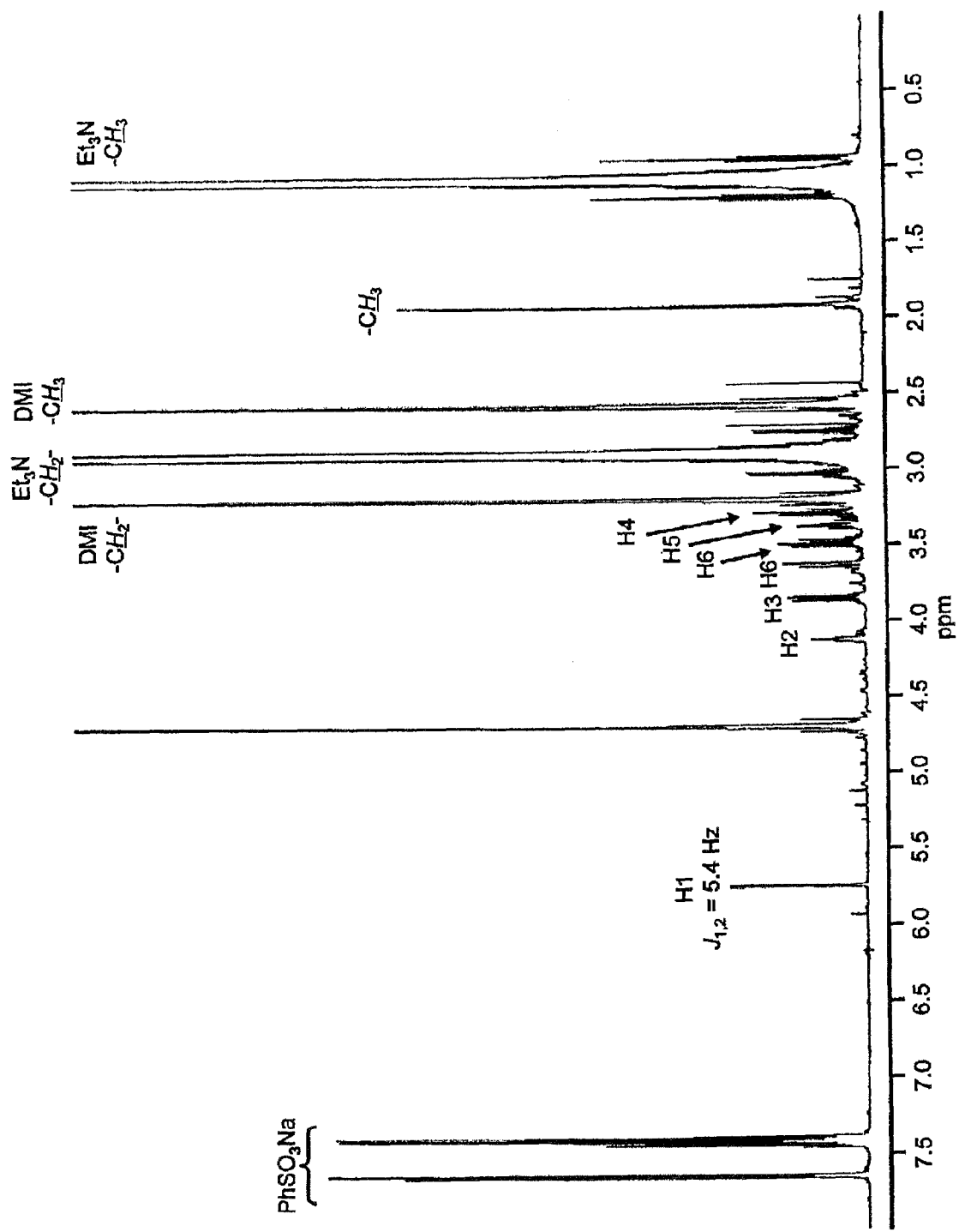
FIG. 3 is the $^1$H-NMR spectrum of the target compound-containing reaction solution obtained in Working Example 2, wherein DMI is 1,3-dimethyl-2-imidazolidinone, $Et_3N$ is triethylamine, and $PhSO_3Na$ is sodium benzenesulfonate.
Figure 4:
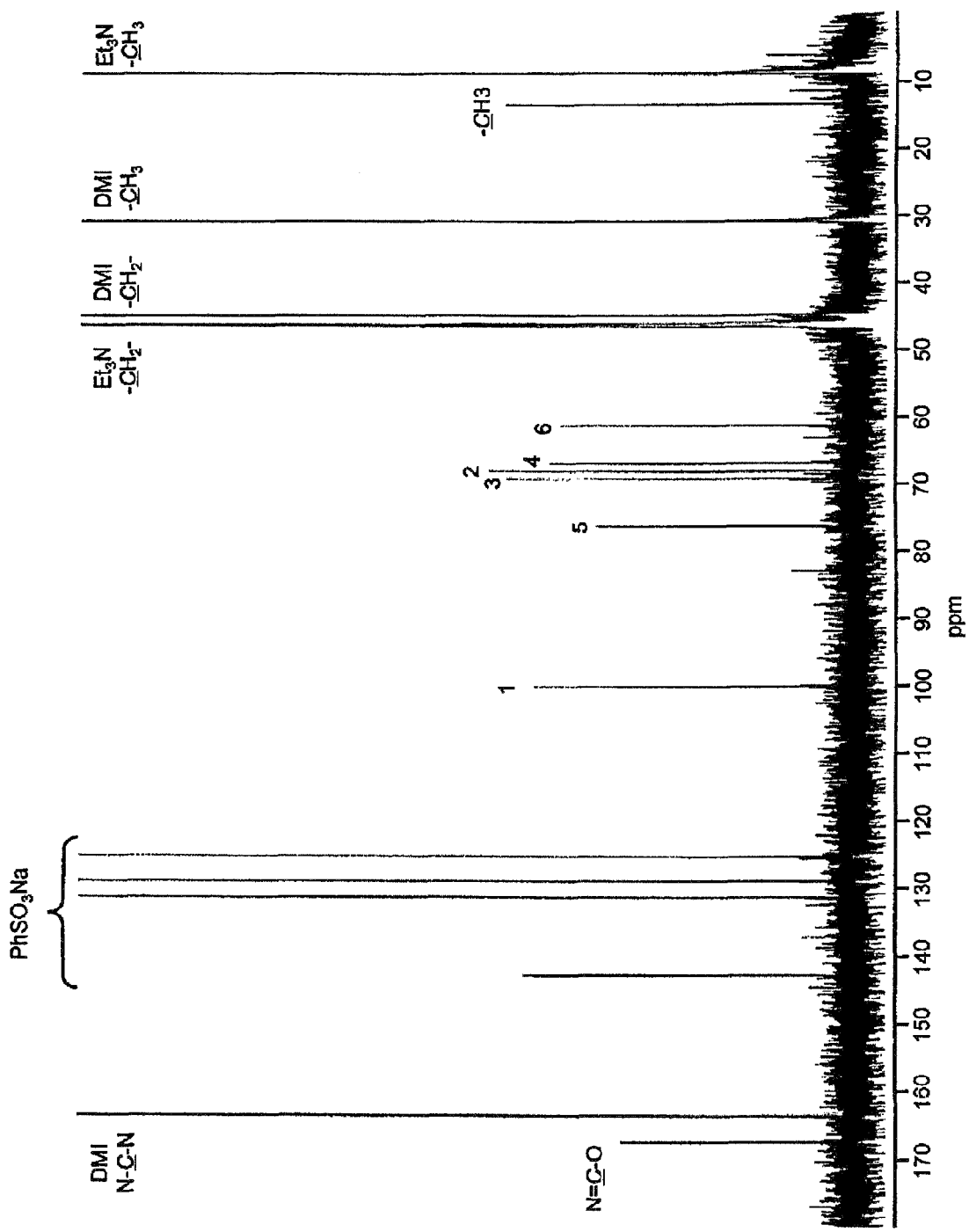
FIG. 4 is the $^{13}$C-NMR spectrum of the target compound-containing reaction solution obtained in Working Example 2, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 3 shows the $^1$H-NMR spectrum and FIG. 4 shows the $^{13}$C-NMR spectrum of the reaction solution containing the target compound.

WORKING EXAMPLE 3

To 42.2 mg (0.250 mmol) of 2-chloro-1,3-dimethylimidazolinium chloride was added 10.4 mg (24.5 µmol) of N,N'-diacetylchitobiose, 104 µL (0.750 mmol) of triethylamine, and 500 µL of deuterated water and the resultant mixture was stirred for one hour at room temperature. When this reaction solution was analyzed by NMR, it was verified that an N,N'-diacetylchitobiose oxazoline derivative of the following formula:

[Chemical Formula 9]

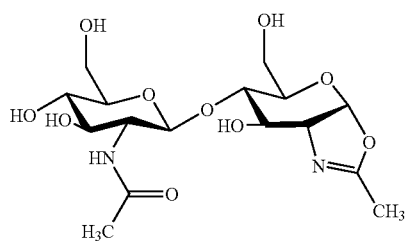

was obtained (yield: 77%).

Figure 5:
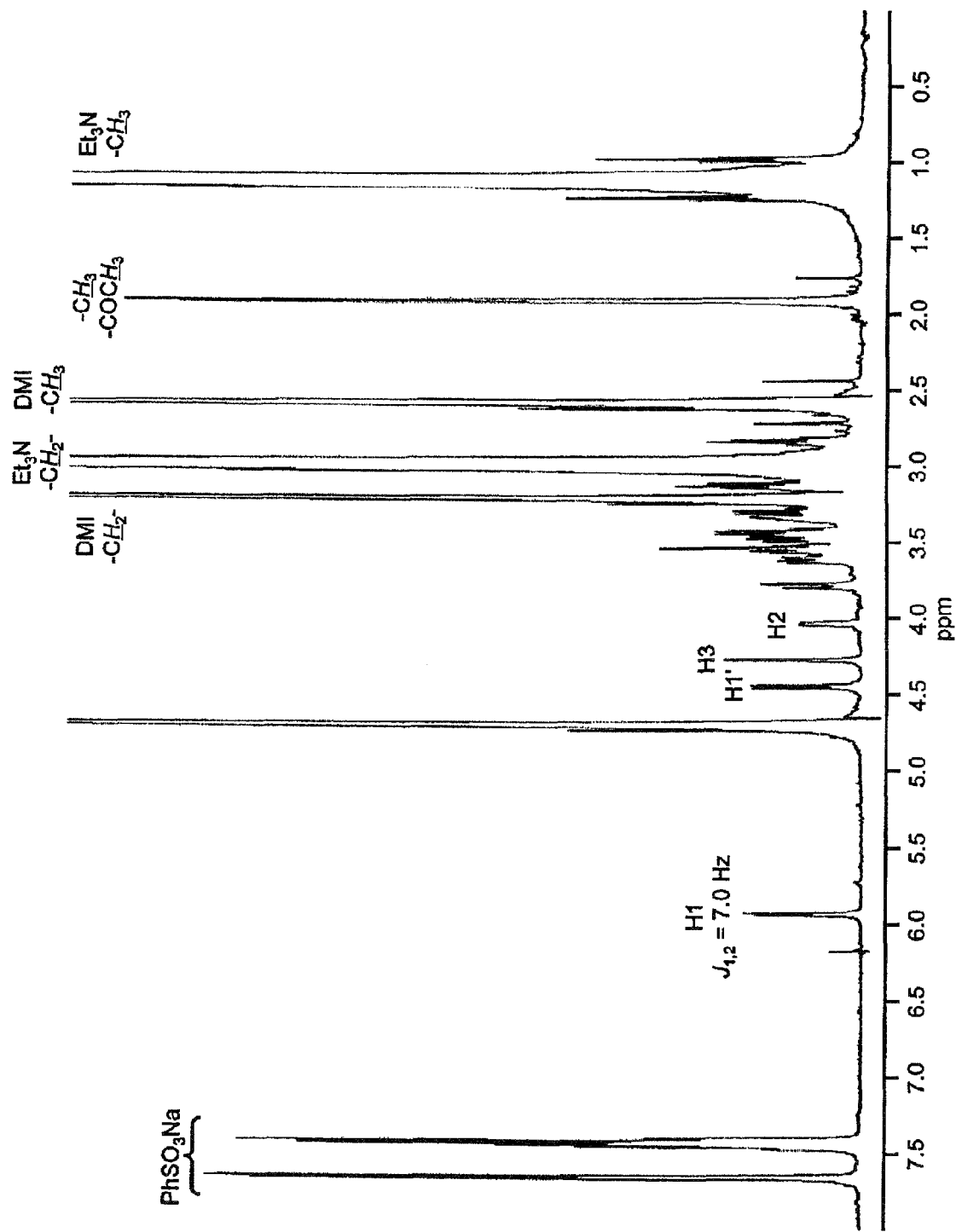
FIG. 5 is the $^1$H-NMR spectrum of the target compound-containing reaction solution obtained in Working Example 3, wherein DMI is 1,3-dimethyl-2-imidazolidinone, $Et_3N$ is triethylamine, and $PhSO_3Na$ is sodium benzenesulfonate.
Figure 6:
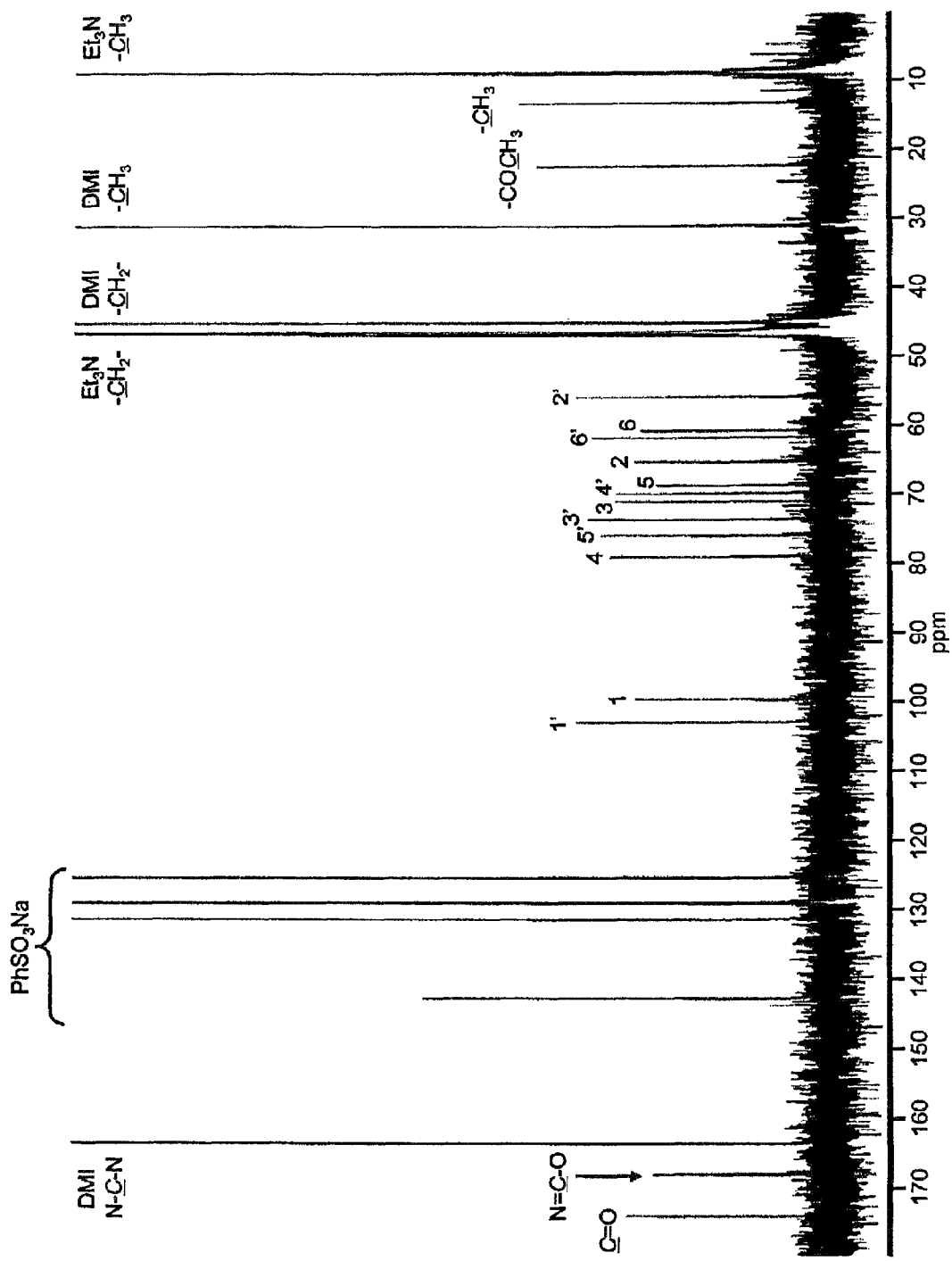
FIG. 6 is the $^{13}$C-NMR spectrum of the target compound-containing reaction solution obtained in Working Example 3, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 5 shows the $^1$H-NMR spectrum and FIG. 6 shows the $^{13}$C-NMR spectrum of the reaction solution containing the target compound.

WORKING EXAMPLE 4

To 42.5 mg (0.251 mmol) of 2-chloro-1,3-dimethylimidazolinium chloride was added 9.8 mg (25.6 μmol) of N-acetyllactosamine, 104 μL (0.750 mmol) of triethylamine, and 500 μL of deuterated water and the resultant mixture was stirred for one hour at room temperature. When this reaction solution was analyzed by NMR, it was verified that an N-acetyllactosamine oxazoline derivative of the following formula:

[Chemical Formula 10]

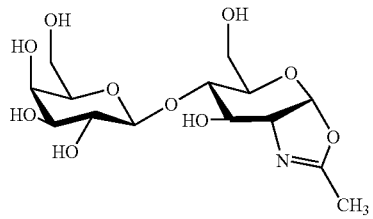

was obtained (yield: 90%).

Figure 7:
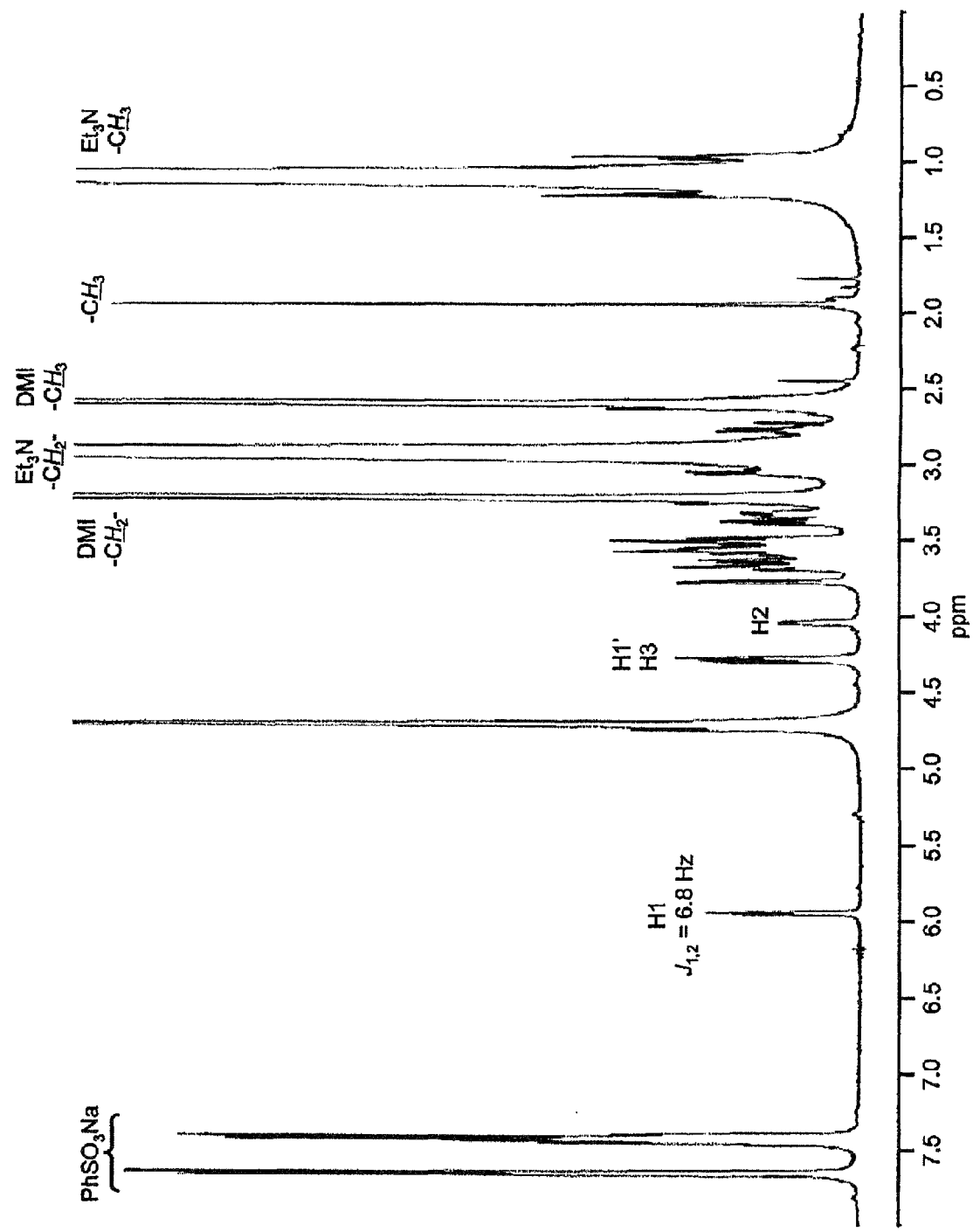
FIG. 7 is the $^1$H-NMR spectrum of the target compound-containing reaction solution obtained in Working Example 4, wherein DMI is 1,3-dimethyl-2-imidazolidinone, $Et_3N$ is triethylamine, and $PhSO_3Na$ is sodium benzenesulfonate.
Figure 8:
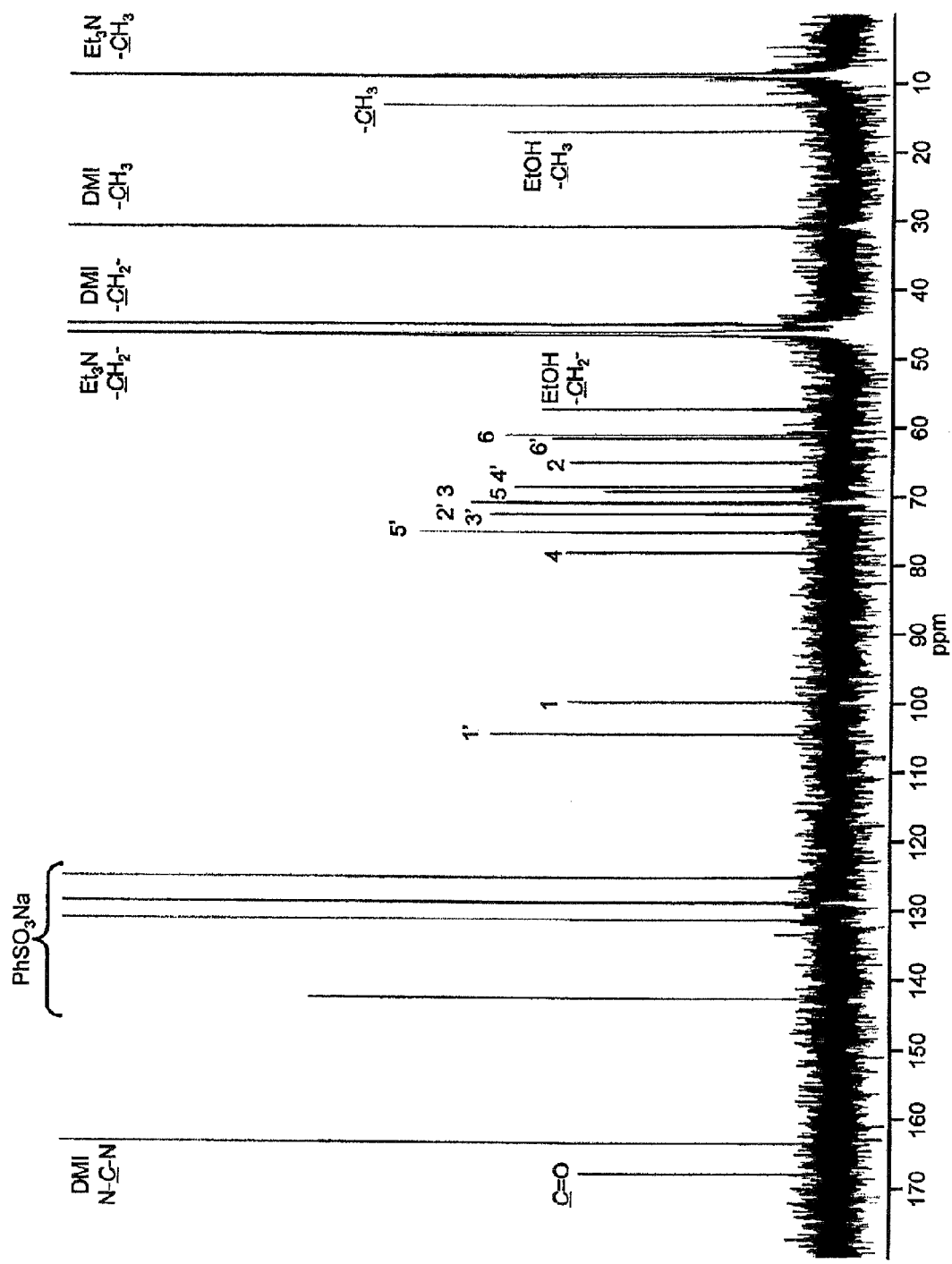
FIG. 8 is the $^{13}$C-NMR spectrum of the target compound-containing reaction solution obtained in Working Example 4, wherein DMI is 1,3-dimethyl-2-imidazolidinone, $Et_3N$ is triethylamine, $PhSO_3Na$ is sodium benzenesulfonate, and EtOH is ethanol.

The yield of the target compound was calculated from the area ratio of the $^1$H-NMR spectrum after adding sodium benzenesulfonate to the reaction solution as a reference standard. FIG. 7 shows the $^1$H-NMR spectrum and FIG. 8 shows the $^{13}$C-NMR spectrum of the reaction solution containing the target compound. A peak derived from the ethanol contained in the starting material N-acetyllactosamine can be verified in the $^{13}$C-NMR spectrum, but it did not contribute in any way in the reaction.

WORKING EXAMPLE 5

To 12.2 mg (72.2 μmol) of 2-chloro-1,3-dimethylimidazolinium chloride was added 3.1 mg (4.9 μmol) of N,N',N''-triacetylchitotriose, 31.0 μL (0.224 mmol) of triethylamine, and 500 μL of deuterated water and the resultant mixture was stirred for one hour at room temperature. When this reaction solution was analyzed by NMR, it was verified that an N,N',N''-triacetylchitotriose oxazoline derivative of the following formula:

[Chemical Formula 11]

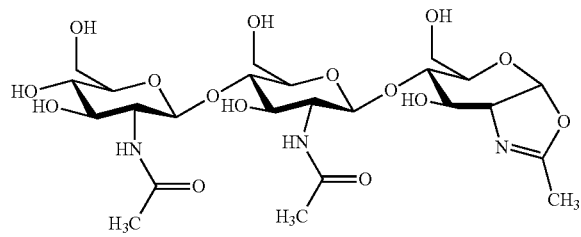

was obtained (yield: 75%).

Figure 9:
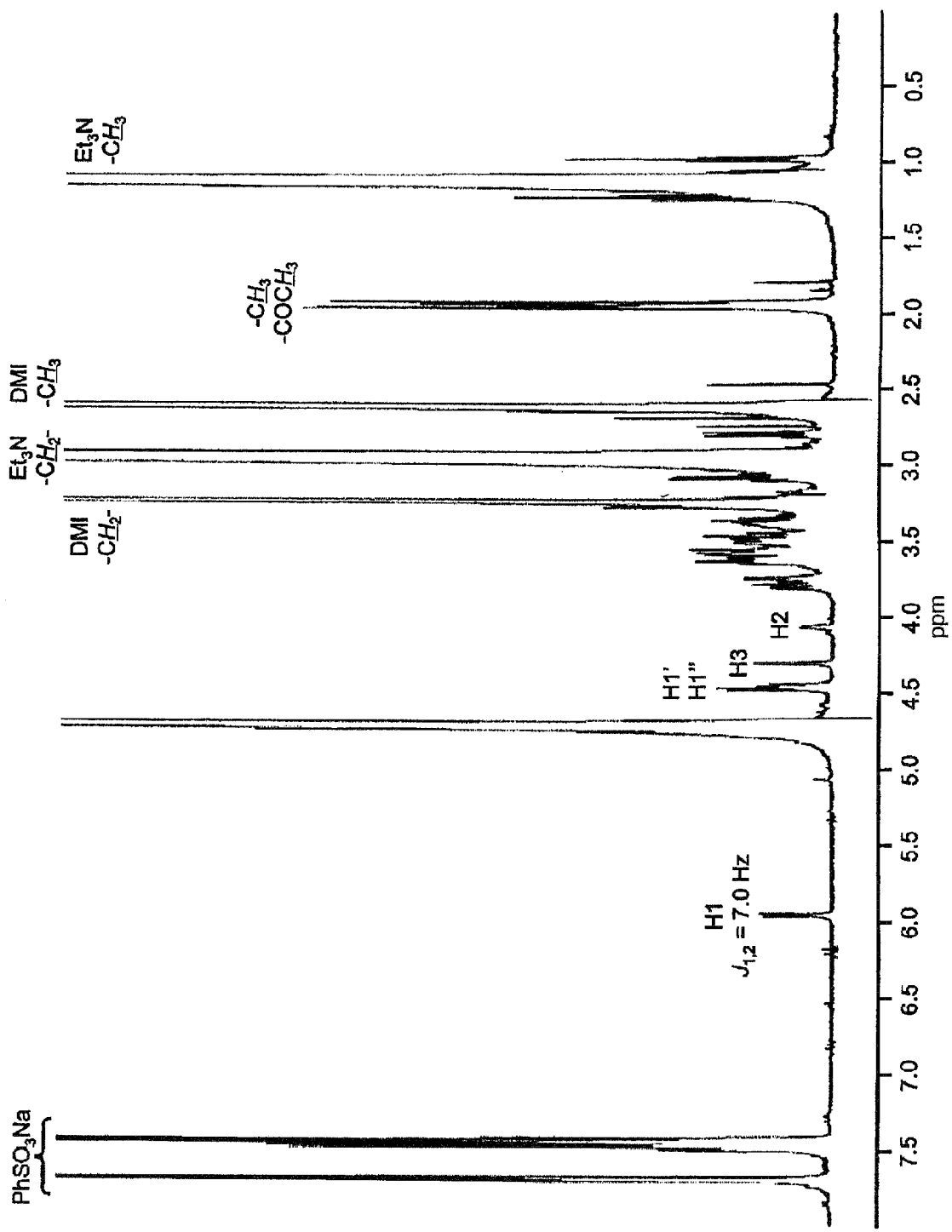
FIG. 9 is the $^1$H-NMR spectrum of the target compound-containing reaction solution obtained in Working Example 5, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 9 shows the $^1$H-NMR spectrum of the reaction solution containing the target compound.

WORKING EXAMPLE 6

To 13.8 mg (81.6 μmol) of 2-chloro-1,3-dimethylimidazolinium chloride was added 4.2 mg (5.06 μmol) of N,N',N'',N'''-tetraacetylchitotetraose, 31.0 μL (0.224 mmol) of triethylamine, and 500 μL of deuterated water and the resultant mixture was stirred for one hour at room temperature. When this reaction solution was analyzed by NMR it was verified that an N,N',N'',N'''-tetraacetyl-chitotetraose oxazoline derivative of the following formula:

[Chemical Formula 12]

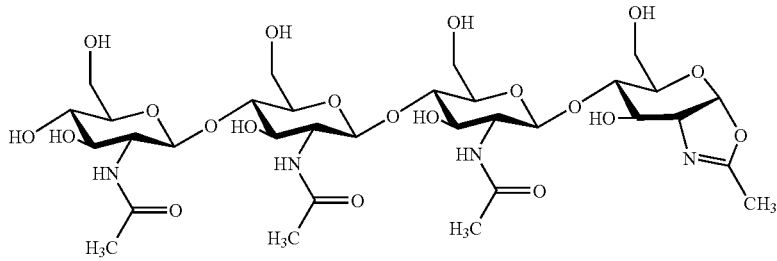

was obtained (yield: 83%).

Figure 10:
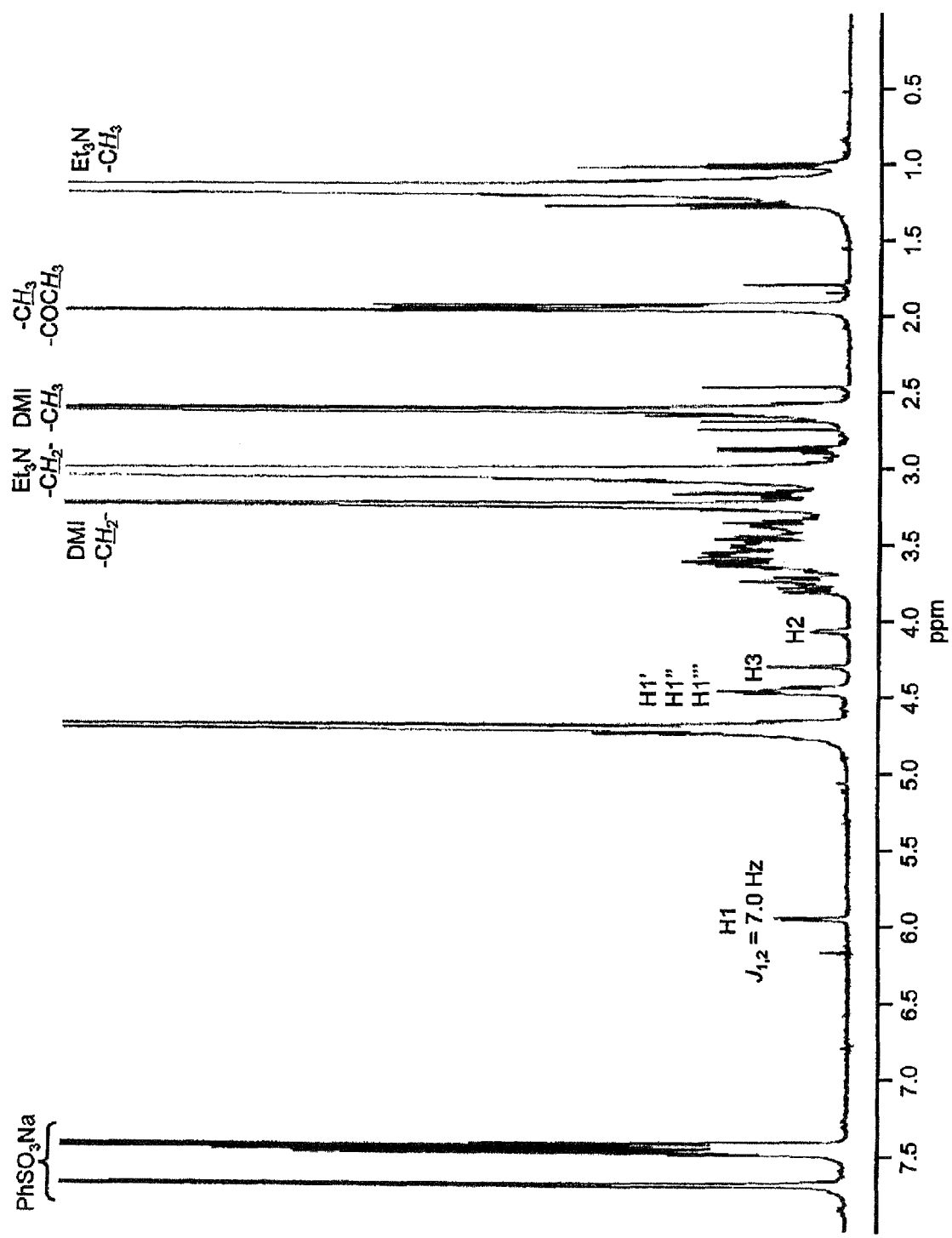
FIG. 10 is the $^1$H-NMR spectrum of the target compound-containing reaction solution obtained in Working Example 6, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 10 shows the $^1$H-NMR spectrum of the reaction solution containing the target compound.

WORKING EXAMPLE 7

To 13.7 mg (81.0 μmol) of 2-chloro-1,3-dimethylimidazolinium chloride was added 5.2 mg (4.93 μmol) of N,N',N'',N''',N''''-pentaacetylchitopentaose, 31.0 μL (0.224 mmol) of triethylamine, and 500 μL of deuterated water and the resultant mixture was stirred for one hour at room temperature. When this reaction solution was analyzed by NMR it was verified that an N,N',N'',N''',N''''-pentaacetyl-chitopentaose oxazoline derivative of the following formula:

[Chemical Formula 13]

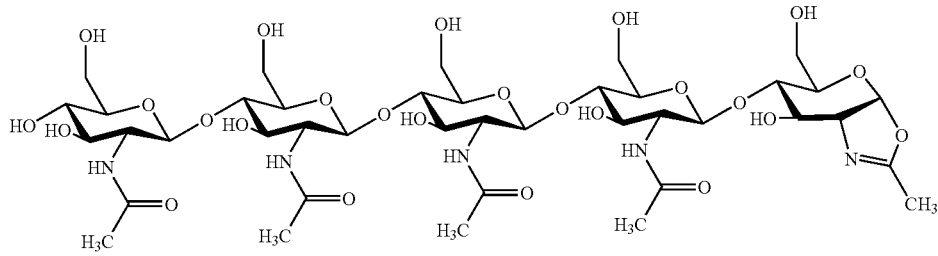

was obtained (yield: 69%).

Figure 11:
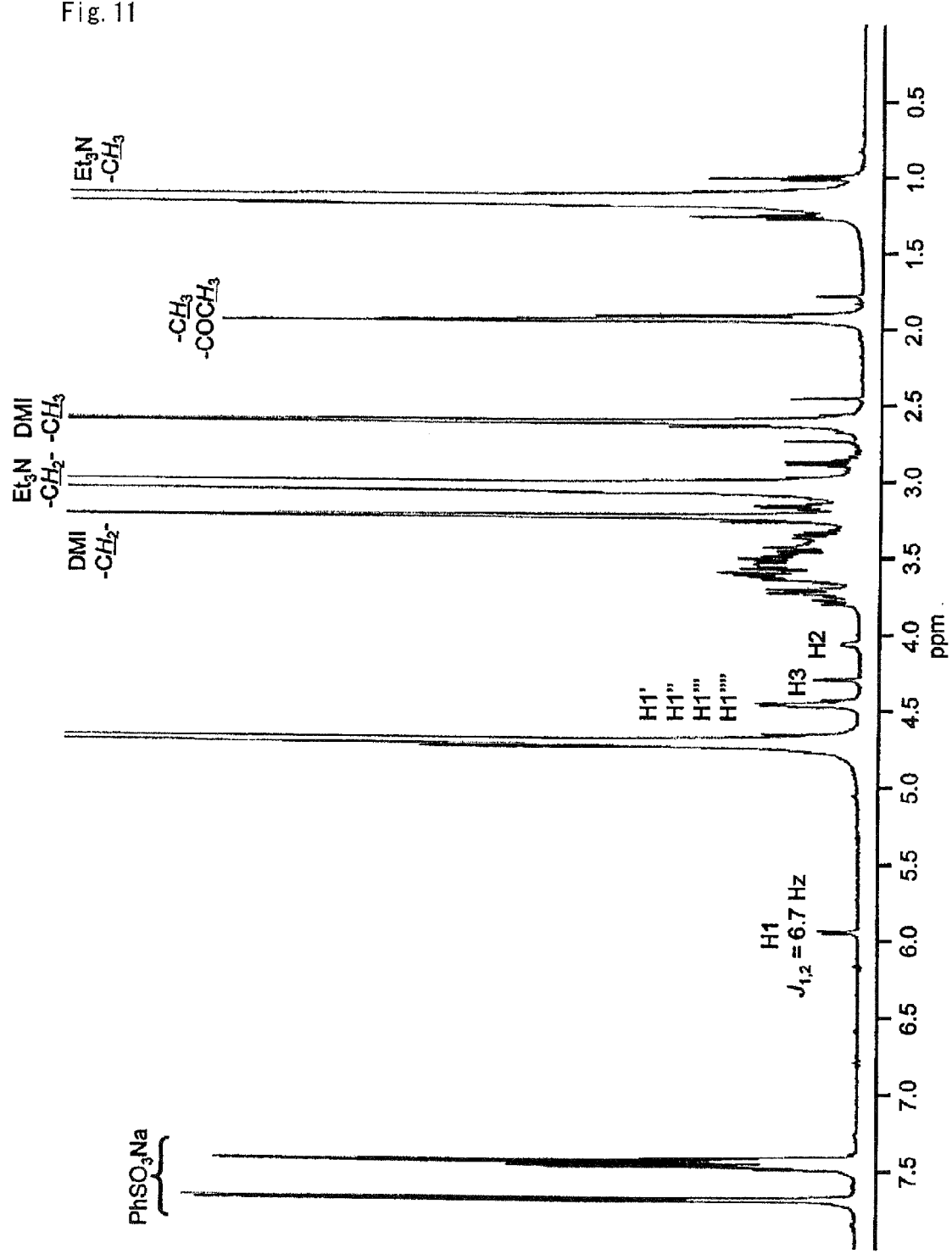
FIG. 11 is the $^1$H-NMR spectrum of the target compound-containing reaction solution obtained in Working Example 7, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 11 shows the $^1$H-NMR spectrum of the reaction solution containing the target compound.

WORKING EXAMPLE 8

To 45.2 mg (0.267 mmol) of 2-chloro-1,3-dimethylimidazolinium chloride was added 26.4 mg (62.2 μmol) of N,N'-diacetylchitobiose, 104 μL (0.750 mmol) of triethylamine, and 250 μL of water and the resultant mixture was stirred for one hour at 0° C. Next, high-performance liquid chromatography was carried out under the following conditions using the reaction solution obtained, and the fraction of the target compound was recovered.
Column: "Inertsil ODS-3 (10.0×250 mm)" (trade name, made by GL Sciences)
Solvent: 100% water
Temperature: 30° C.
Flow rate: 4.8 mL/min
Detector: UV (214 nm)

The fraction obtained was freeze dried to afford an N,N'-diacetylchitobiose oxazoline derivative of the following formula:

[Chemical Formula 14]

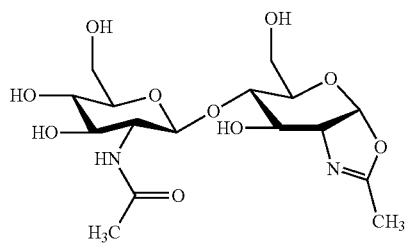

(23.3 mg, yield: 92%).

The structure of the above oxazoline derivative of N,N'-diacetylchitobiose was confirmed by $^1$H-NMR.

WORKING EXAMPLE 9

To 16.6 mg (98.2 μmol) of 2-chloro-1,3-dimethylimidazolinium chloride was added 10.2 mg of a high-mannose sugar chain, 40.4 μL (0.291 mmol) of triethylamine, and 194 μL of deuterated water and the resultant mixture was stirred for one hour at 0° C. When this reaction solution was analyzed by NMR, it was verified that a high-mannose sugar chain oxazoline derivative was obtained (yield: 64%). A typical structure of the target compound is shown by the following formula:

[Chemical Formula 15]

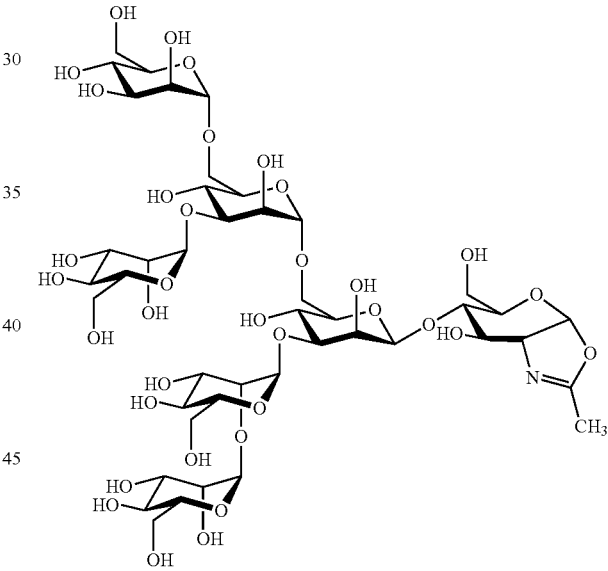

Figure 12:
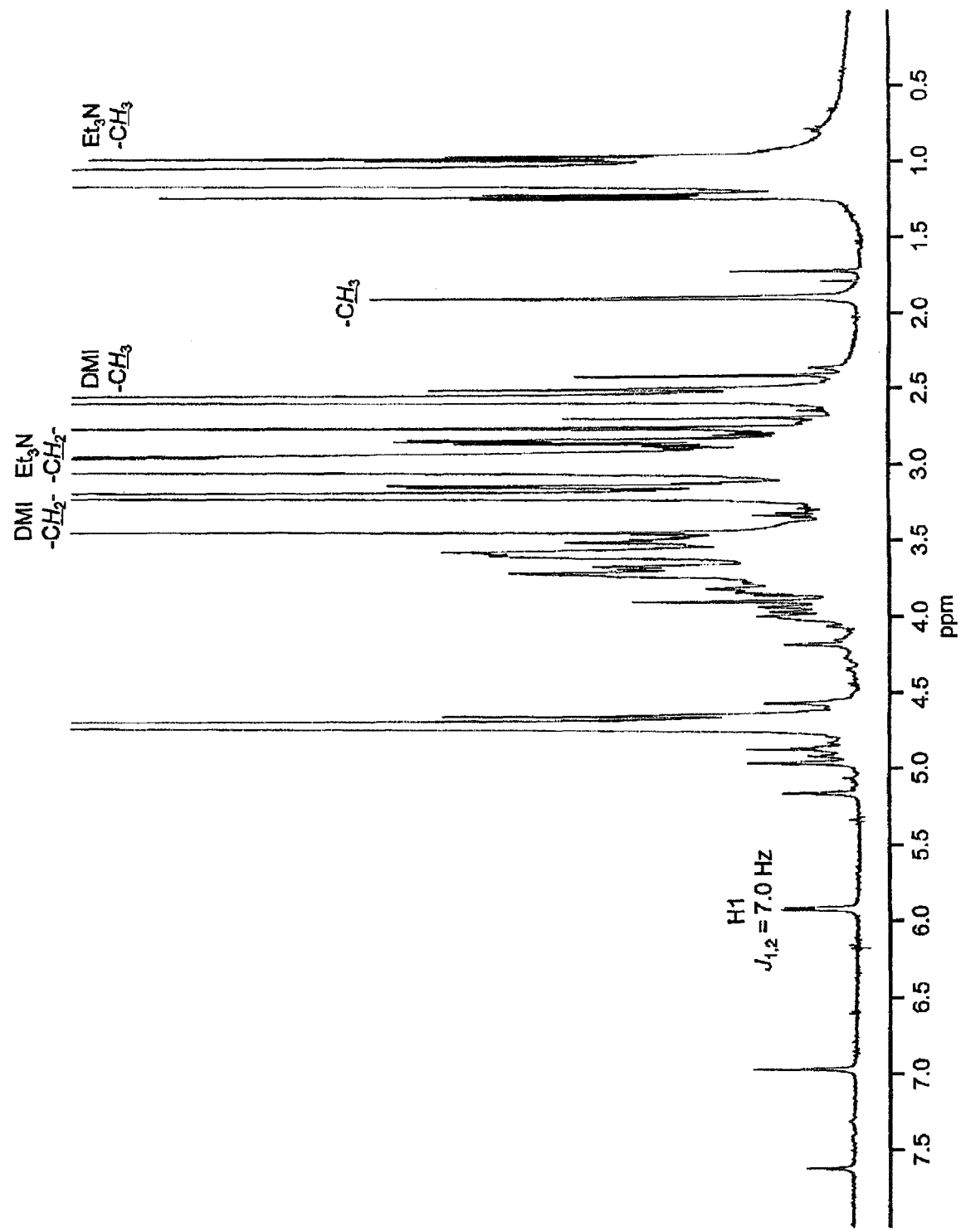
FIG. 12 is the $^1$H-NMR spectrum of the target compound-containing reaction solution obtained in Working Example 9, wherein DMI is 1,3-dimethyl-2-imidazolidinone, and $Et_3N$ is triethylamine.

The yield of the target compound was calculated from the area ratio of the $^1$H-NMR spectrum. FIG. 12 shows the $^1$H-NMR spectrum of the reaction solution containing the target compound. A high-mannose sugar chain obtained by refining by gel permeation column chromatography a sugar chain obtained by treatment by endo-β-N-acetylglucosaminidase derived from *Arthrobacter protophormiae* using ovalbumin as the starting material was used as the high-mannose sugar chain.

WORKING EXAMPLE 10

To 17.6 mg (0.104 mmol) of 2-chloro-1,3-dimethylimidazolinium chloride was added 20.0 mg (9.9 μmol) of a sialo complex-type sugar chain, 42.0 μL (0.303 mmol) of triethylamine, and 200 μL of deuterated water and the resultant mixture was stirred for one hour at 0° C. When this reaction solution was analyzed by NMR, it was verified that a sialo complex-type sugar chain oxazoline derivative of the following formula:

[Chemical Formula 16]

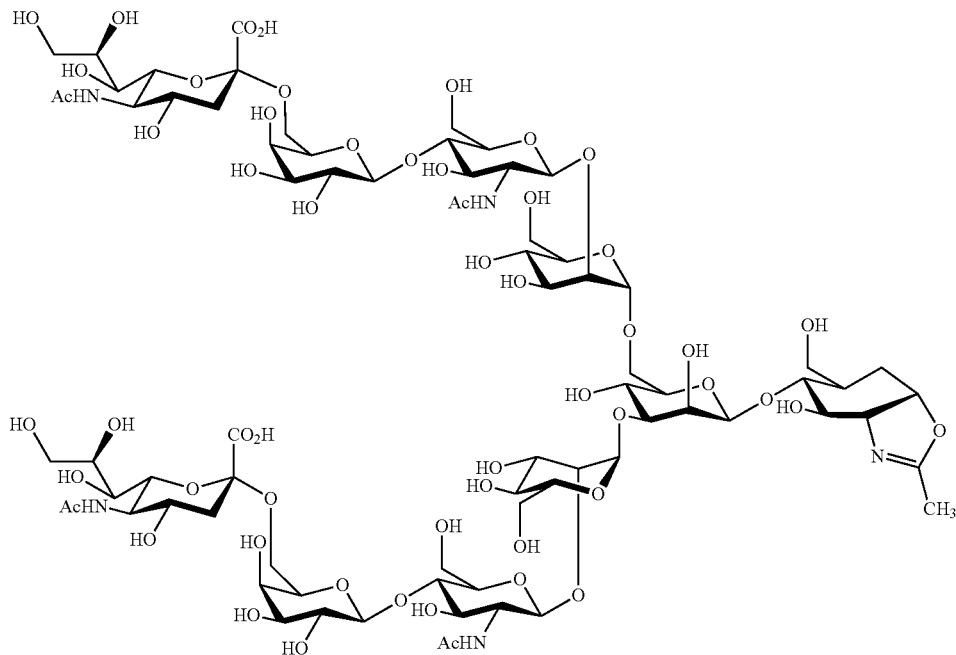

was obtained (yield: 92%).

Figure 13:
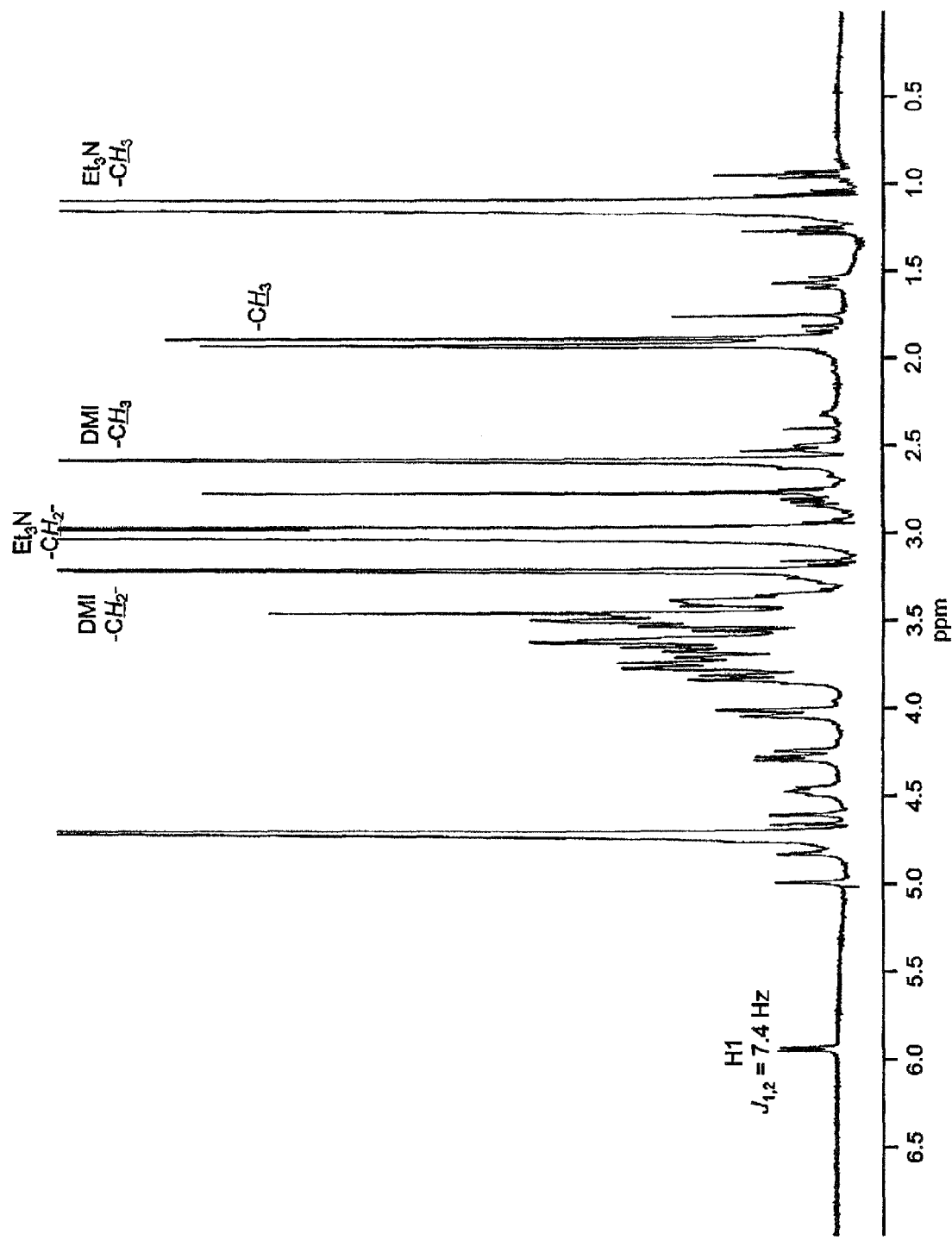
FIG. 13 is the $^1$H-NMR spectrum of the target compound-containing reaction solution obtained in Working Example 10, wherein DMI is 1,3-dimethyl-2-imidazolidinone, and $Et_3N$ is triethylamine.

The yield of the target compound was calculated from the area ratio of the $^1$H-NMR spectrum. FIG. 13 shows the $^1$H-NMR spectrum of the reaction solution containing the target compound. A sialo complex-type sugar chain obtained by refining by high-performance liquid chromatography a sugar chain obtained by treatment by endo-β-N-acetylglucosaminidase derived from *Mucor hiemalis* using a sugar chain bonded to Fmoc-asparagine as the starting material was used as the sialo complex-type sugar chain.

Other oxazoline derivatives of sialo complex-type sugars can be synthesized in the same way. Sialo complex-type sugar chains are oligosaccharides having two sialic acids on each non-reducing end and can be utilized for various purposes such as the production of sugar chips and the like. This showed that the method of the present invention allows oxazolination of even carboxylic acids present in the sialic acid moiety basically quantitatively without requiring any protection.

WORKING EXAMPLE 11

To 63.4 mg (0.375 mmol) of 2-chloro-1,3-dimethylimidazolinium chloride was added 27.7 mg (0.125 mmol) of N-acetylglucosamine, 156 μL (1.13 mmol) of triethylamine, and 500 μL of deuterated water and the resultant mixture was stirred for 15 minutes at 0° C. When this reaction solution was analyzed by NMR, it was verified that an N-acetyl-glucosamine oxazoline derivative of the following formula:

[Chemical Formula 17]

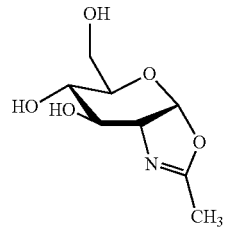

was obtained (yield: 90%).

Figure 14:
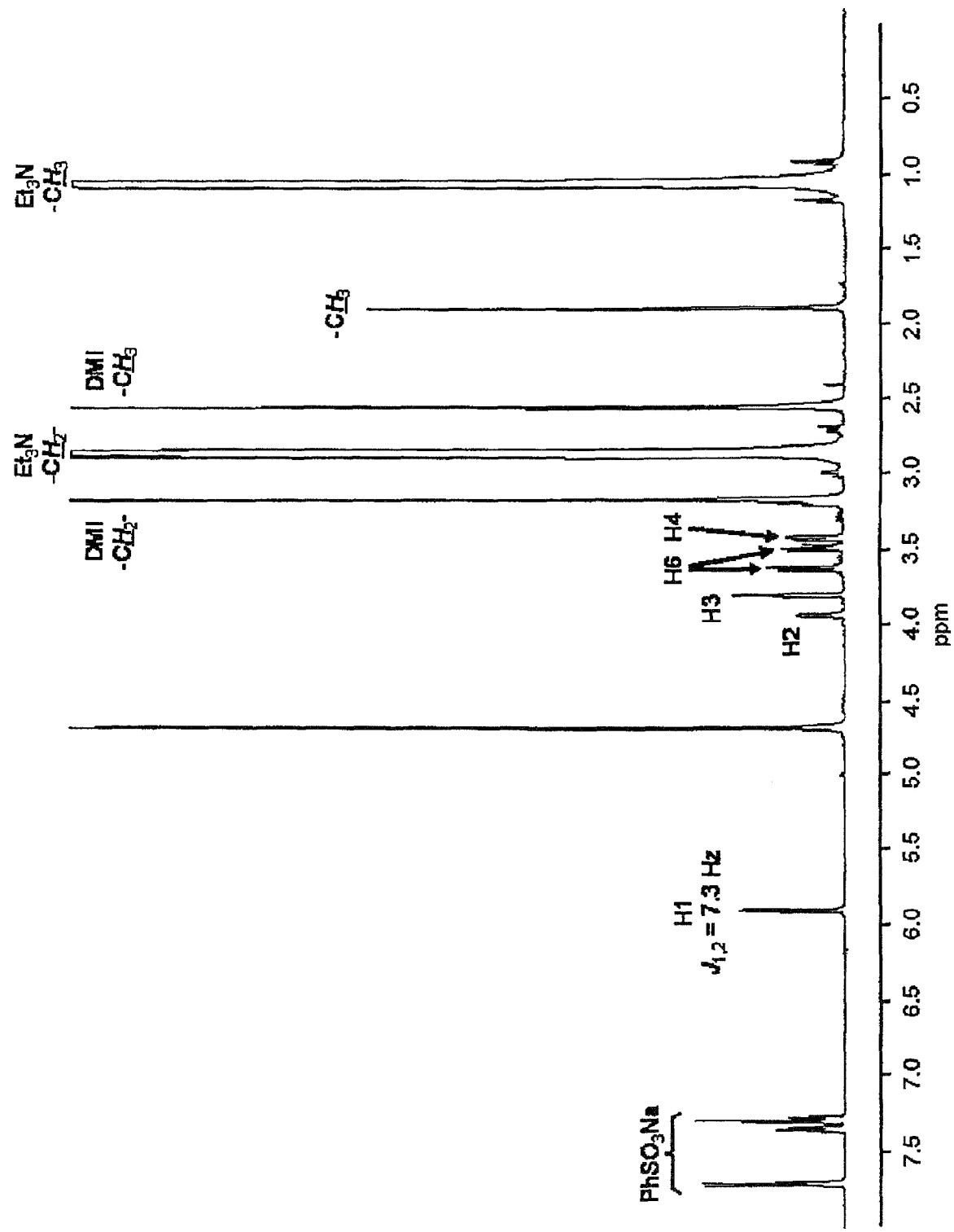
FIG. 14 is the $^1$H-NMR spectrum of the target compound-containing reaction solution obtained in Working Example 11, wherein DMI is 1,3-dimethyl-2-imidazolidinone, $Et_3N$ is triethylamine, and $PhSO_3Na$ is sodium benzenesulfonate.

The yield of the target compound was calculated from the area ratio of the $^1$H-NMR spectrum after adding sodium benzenesulfonate to the reaction solution as a reference standard. FIG. 14 shows the $^1$H-NMR spectrum of the reaction solution containing the target compound.

WORKING EXAMPLE 12

To 63.4 mg (0.375 mmol) of 2-chloro-1,3-dimethylimidazolinium chloride was added 27.7 mg (0.125 mmol) of N-acetylglucosamine, 262 μL (1.13 mmol) of a 4.3 M triethylamine aqueous solution, and 238 μL of deuterated water and the resultant mixture was stirred for 15 minutes at 0° C. When this reaction solution was analyzed by NMR, it was verified that an N-acetylglucosamine oxazoline derivative of the following formula:

[Chemical Formula 18]

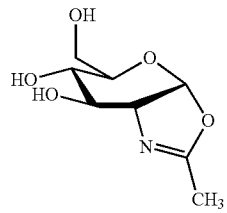

was obtained (yield: 74%).

Figure 15:
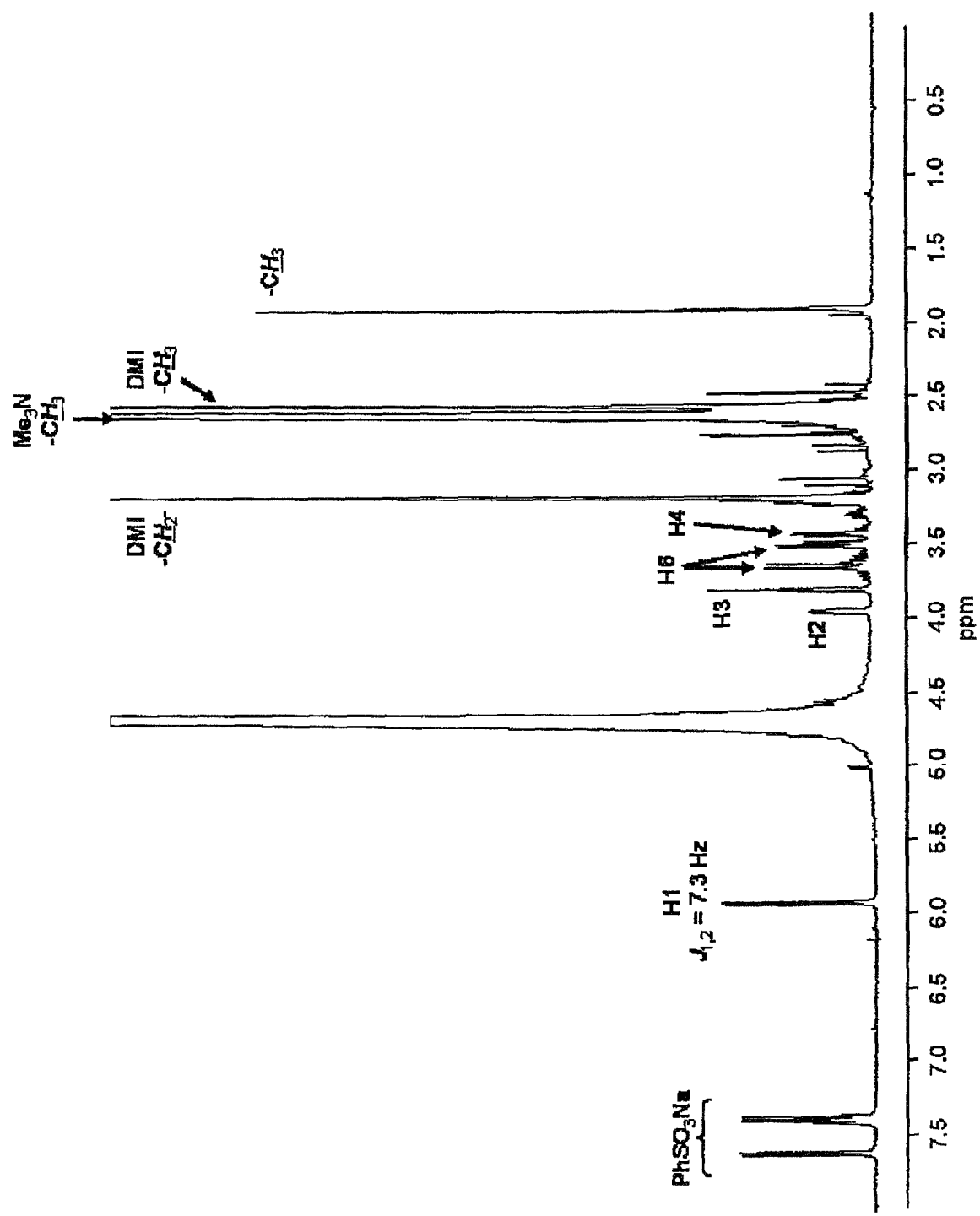
FIG. 15 is the $^1$H-NMR spectrum of the target compound-containing reaction solution obtained in Working Example 12, wherein DMI is 1,3-dimethyl-2-imidazolidinone, $Me_3N$ is trimethylamine, and $PhSO_3Na$ is sodium benzenesulfonate.

The yield of the target compound was calculated from the area ratio of the ¹H-NMR spectrum after adding sodium benzenesulfonate to the reaction solution as a reference standard. FIG. 15 shows the ¹H-NMR spectrum of the reaction solution containing the target compound.

WORKING EXAMPLE 13

To 63.4 mg (0.375 mmol) of 2-chloro-1,3-dimethylimidazolinium chloride was added 27.7 mg (0.125 mmol) of N-acetylglucosamine, 121 μL (1.13 mmol) of N,N-dimethylethylamine, and 500 μL of deuterated water and the resultant mixture was stirred for 15 minutes at 0° C. When this reaction solution was analyzed by NMR, it was verified that an N-acetylglucosamine oxazoline derivative of the following formula:

[Chemical Formula 19]

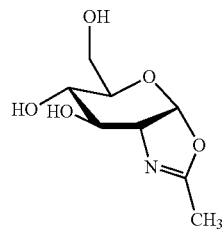

was obtained (yield: 72%).

Figure 16:
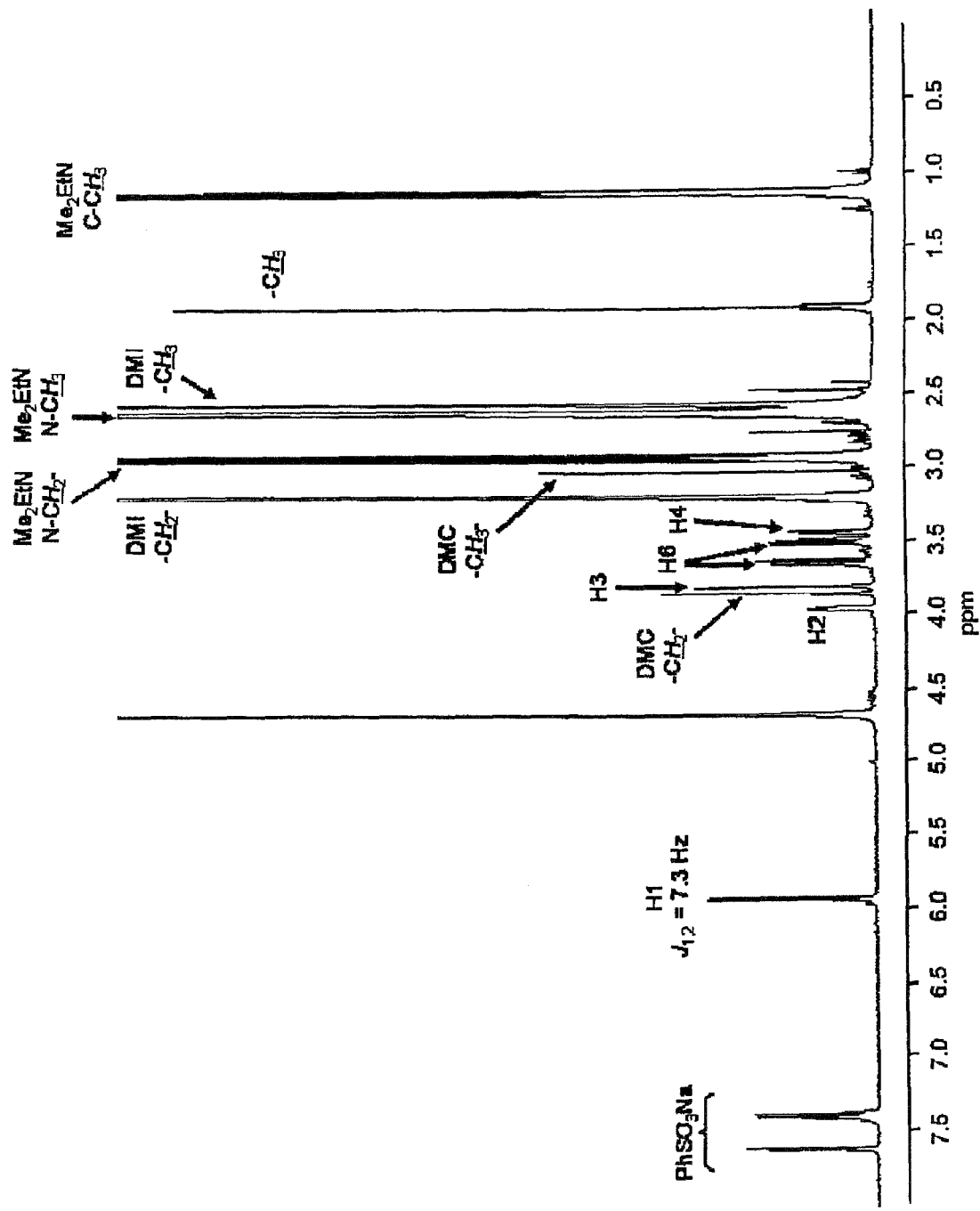
FIG. 16 is the $^1$H-NMR spectrum of the target compound-containing reaction solution obtained in Working Example 13, wherein DMI is 1,3-dimethyl-2-imidazolidinone, DMC is 2-chloro-1,3-dimethylimidazolinium chloride, Me$_2$EtN is N,N-dimethylethylamine, and PhSO$_3$Na is sodium benzenesulfonate.

The yield of the target compound was calculated from the area ratio of the ¹H-NMR spectrum after adding sodium benzenesulfonate to the reaction solution as a reference standard. FIG. 16 shows the ¹H-NMR spectrum of the reaction solution containing the target compound.

WORKING EXAMPLE 14

To 63.4 mg (0.375 mmol) of 2-chloro-1,3-dimethylimidazolinium chloride was added 27.7 mg (0.125 mmol) of N-acetylglucosamine, 158 μL (1.13 mmol) of N-n-butyldimethylamine, and 500 μL of deuterated water and the resultant mixture was stirred for 15 minutes at 0° C. When this reaction solution was analyzed by NMR, it was verified that an N-acetylglucosamine oxazoline derivative of the following formula:

[Chemical Formula 20]

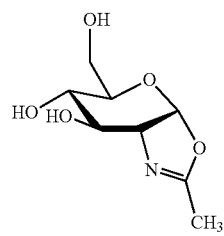

was obtained (yield: 78%).

Figure 17:
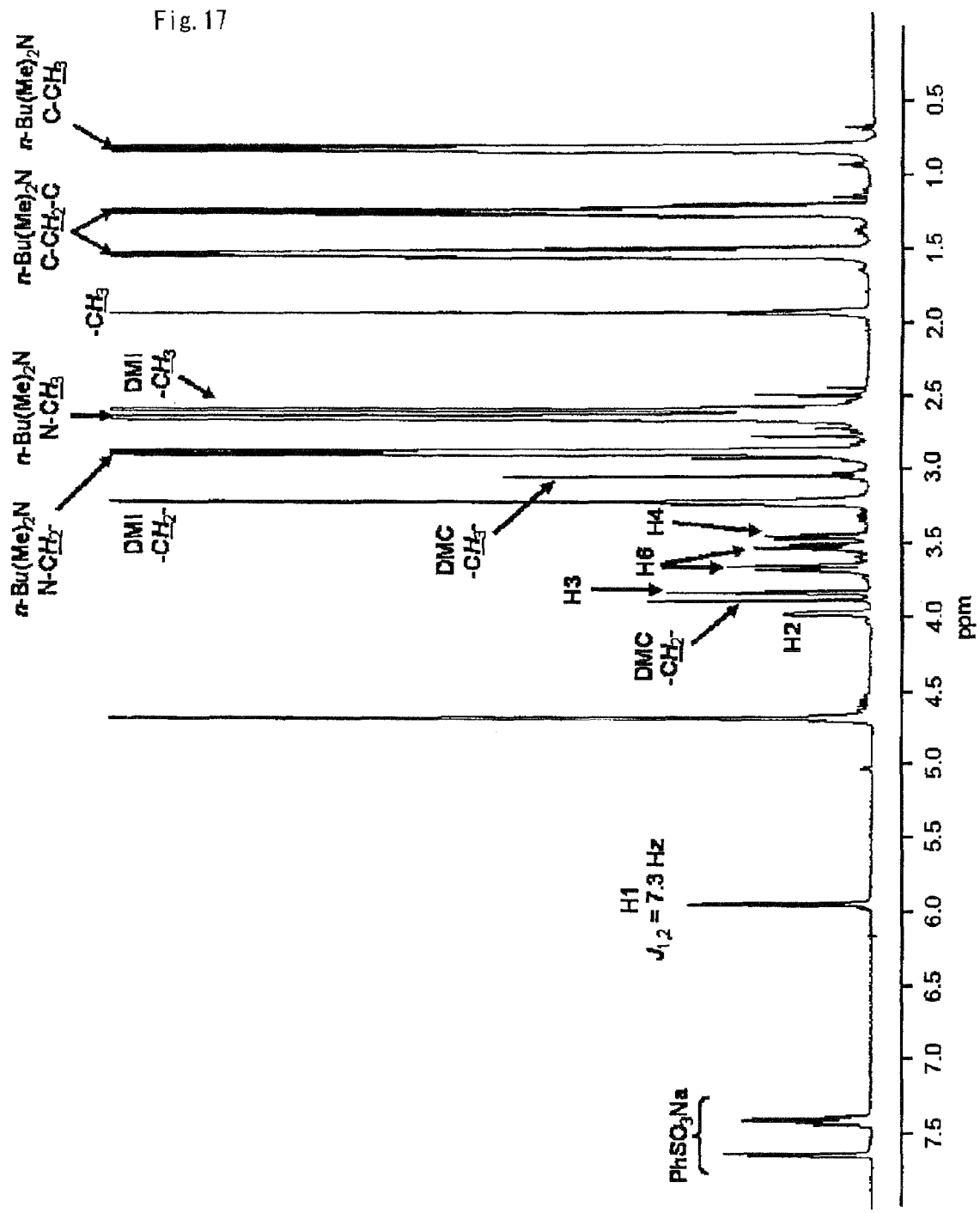
FIG. 17 is the $^1$H-NMR spectrum of the target compound-containing reaction solution obtained in Working Example 14, wherein DMI is 1,3-dimethyl-2-imidazolidinone, DMC is 2-chloro-1,3-dimethylimidazolinium chloride, n-Bu(Me)$_2$N is N-n-butyldimethylamine, and PhSO$_3$Na is sodium benzenesulfonate.

The yield of the target compound was calculated from the area ratio of the ¹H-NMR spectrum after adding sodium benzenesulfonate to the reaction solution as a reference standard. FIG. 17 shows the ¹H-NMR spectrum of the reaction solution containing the target compound.

WORKING EXAMPLE 15

To 63.4 mg (0.375 mmol) of 2-chloro-1,3-dimethylimidazolinium chloride was added 27.7 mg (0.125 mmol) of N-acetylglucosamine, 192 μL (1.13 mmol) of N,N-diisopropylethylamine, and 500 μL of deuterated water and the resultant mixture was stirred for 15 minutes at 0° C. When this reaction solution was analyzed by NMR, it was verified that an N-acetylglucosamine oxazoline derivative of the following formula:

[Chemical Formula 21]

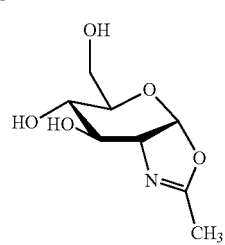

was obtained (yield: 61%).

Figure 18:
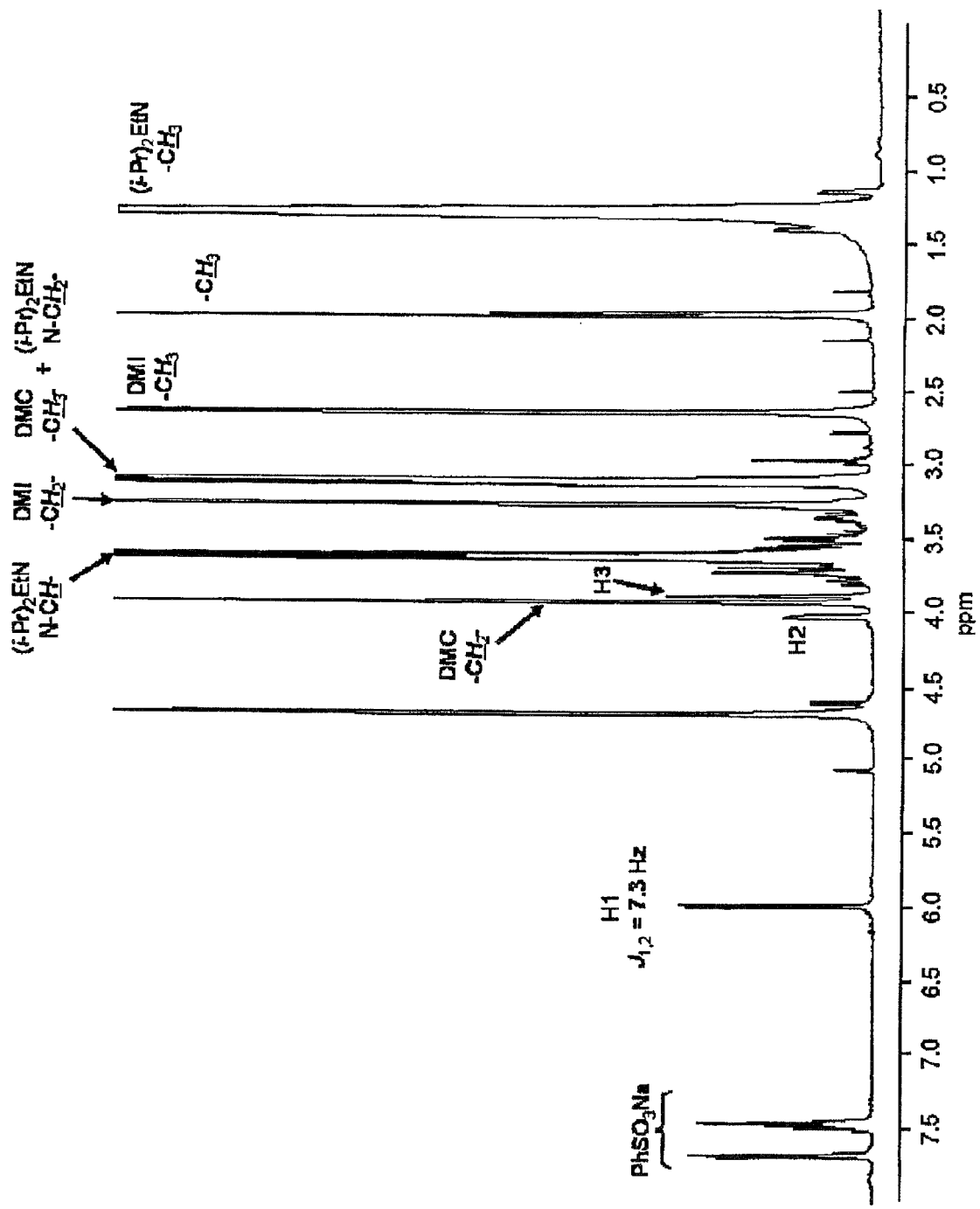
FIG. 18 is the $^1$H-NMR spectrum of the target compound-containing reaction solution obtained in Working Example 15, wherein DMI is 1,3-dimethyl-2-imidazolidinone, DMC is 2-chloro-1,3-dimethylimidazolinium chloride, (i-Pr)$_2$EtN is N,N-diisopropylethylamine, and PhSO$_3$Na is sodium benzenesulfonate

The yield of the target compound was calculated from the area ratio of the ¹H-NMR spectrum after adding sodium benzenesulfonate to the reaction solution as a reference standard. FIG. 18 shows the ¹H-NMR spectrum of the reaction solution containing the target compound.

WORKING EXAMPLE 16

To 63.4 mg (0.375 mmol) of 2-chloro-1,3-dimethylimidazolinium chloride was added 27.7 mg (0.125 mmol) of N-acetylglucosamine, 173 μL (1.13 mmol) of N,N,N',N'-tetramethylethylenediamine, and 500 μL of deuterated water and the resultant mixture was stirred for 15 minutes at 0° C. When this reaction solution was analyzed by NMR, it was verified that an N-acetylglucosamine oxazoline derivative of the following formula:

[Chemical Formula 22]

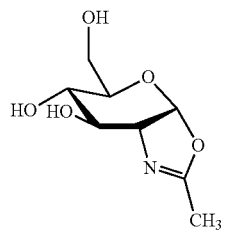

was obtained (yield: 45%).

Figure 19:
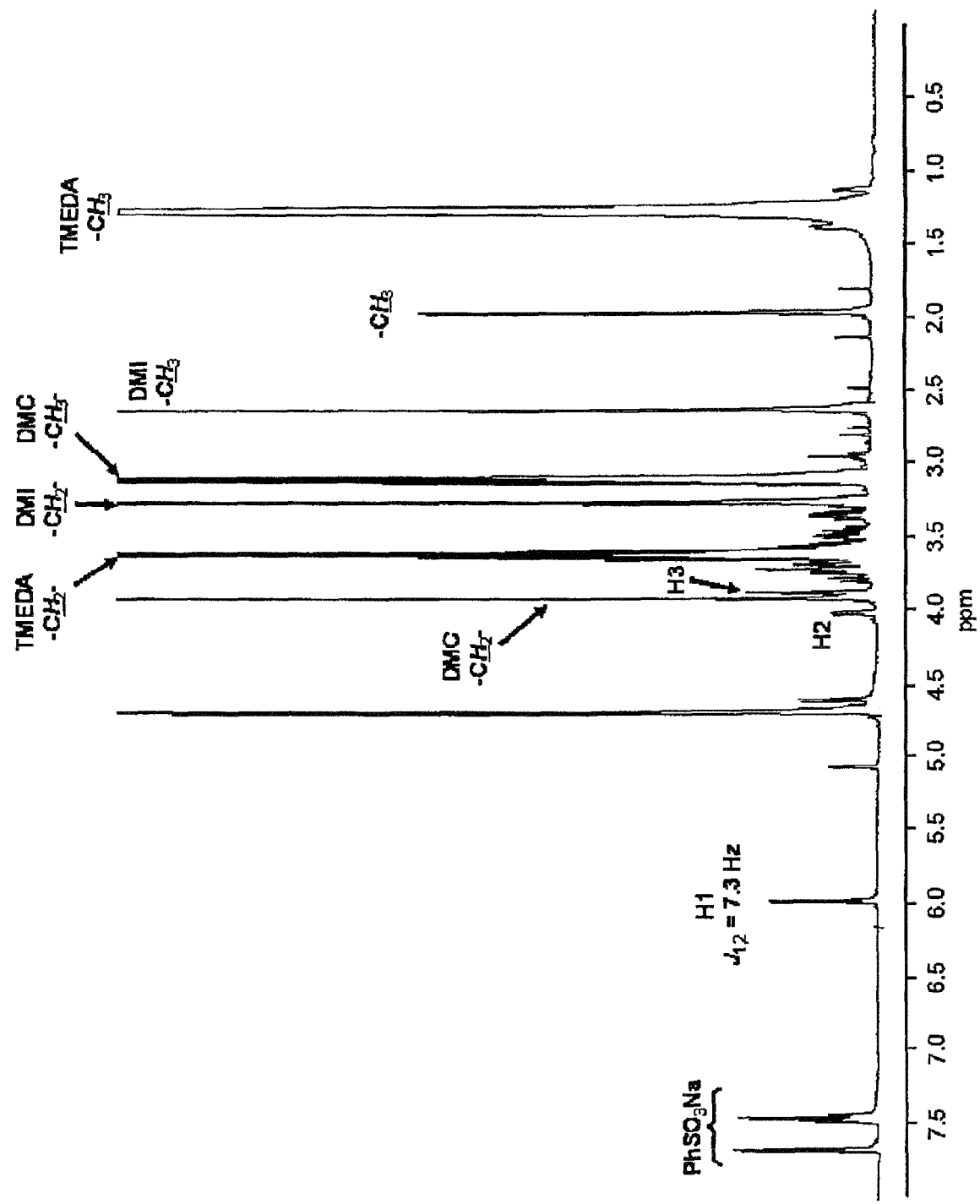
FIG. 19 is the $^1$H-NMR spectrum of the target compound-containing reaction solution obtained in Working Example 16, wherein DMI is 1,3-dimethyl-2-imidazolidinone, DMC is 2-chloro-1,3-dimethylimidazolinium chloride, TMEDA is N,N,N',N'-tetramethylethylenediamine, and PhSO$_3$Na is sodium benzenesulfonate.

The yield of the target compound was calculated from the area ratio of the $^1$H-NMR spectrum after adding sodium benzenesulfonate to the reaction solution as a reference standard. FIG. 19 shows the $^1$H-NMR spectrum of the reaction solution containing the target compound.

COMPARATIVE EXAMPLE 1

To 335 mg (1.75 mmol) of 1-[3-(dimethylamino)propyl]-3-ethyl carbodiimide hydrochloride was added 55 mg (0.25 mmol) of N-acetylglucosamine, 35 μL (0.25 mmol) of triethylamine, and 500 μL of deuterated water and the resultant mixture was stirred for 4 days at 4° C. When this reaction solution was analyzed by NMR, it was verified that the target compound, 2-methyl(1,2-dideoxy-α-D-glucopyrano)[2,1-d]-2-oxazoline, was obtained (yield: 37%). The yield of the target compound was calculated from the area ratio of the $^1$H-NMR spectrum after adding sodium benzoate to the reaction solution as a reference standard. 1-[3-(Dimethylamino)propyl]-3-ethyl carbodiimide hydrochloride has the following chemical structure:

[Chemical Formula 23]

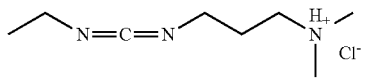

COMPARATIVE EXAMPLE 2

To 37.0 mg (0.134 mmol) of 4-(4,6-dimethoxy-1,3,5-triazin-2-yl)-4-methylmorpholinium chloride hydrate was added 5.6 mg (25.3 μmol) of N-acetylglucosamine, 21.8 μL (0.125 mmol) of N,N-diisopropylethylamine, and 500 μL of deuterated water and the resultant mixture was stirred for six hours at room temperature. When this reaction solution was analyzed by NMR, it was verified that the target compound, 2-methyl(1,2-dideoxy-α-D-glucopyrano)[2,1-d]-2-oxazoline, was obtained (yield: 33%). The yield of the target compound was calculated from the area ratio of the $^1$H-NMR spectrum after adding sodium benzoate to the reaction solution as a reference standard. 4-(4,6-Dimethoxy-1,3,5-triazin-2-yl)-4-methylmorpholinium chloride has the following chemical structure:

[Chemical Formula 24]

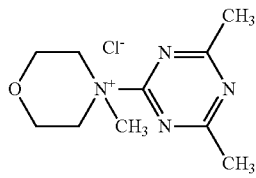

WORKING EXAMPLE 17

To a solution of 4,5-Dihydro-2-methyl{1,2-dideoxy-4-O-(β-D-galactopyranosyl)-α-D-glucopyranosyl}[2,1-d]oxazole (48 mg, 0.13 mmol) and methyl(N-acetyl-β-D-glucosamide) (GlcNAcβ-OMe; 92 mg, 0.39 mmol) in 150 μL of 0.05 M citrate buffer (pH 9.0) was added a solution of chitinase (Bacillus sp., 10 wt % versus the sugar donor oxazoline derivative) in 80 μL of 0.01 M citrate buffer (pH 9.0), and the mixture was stirred for 0.5 hour at 34° C. The enzyme was inactivated by adding THF to the resulting mixture. After distilling off the solvent and dissolving the residue in water, the mixture was separated by HPLC to afford Gal(β1-4)GlcNAc(β1-4)GlcNAcβOMe.

WORKING EXAMPLE 18

To 4,5-dihydro-2-methyl(1,2-dideoxy-4-O-(β-D-galactopyranosyl)-α-D-glucopyranosyl)[2,1-d]oxazole (73 mg, 0.2 mmol) in a microtube was added a 0.05 M Tris buffer (pH 9.0) solution (2.0 mL) of GlcNAcβ-SCH$_2$CH$_2$CONHCH$_2$NHCOCH=CH$_2$ (26 mg, 66.7 mmol) and chitinase (Bacillus sp., 7.3 mg, 292 mU), and the resultant mixture was incubated at 40° C. After adding an excess of THF to the resulting mixture, the enzyme was inactivated by heating the mixture for 20 minutes at 90° C. After distilling off the solvent and dissolving the residue in water, the mixture was refined by HPLC fractionation (Inertsil-ODS, H$_2$O/MeOH, 3.0 mL/min), and Gal(β1-4)GlcNAc(β1-4)GlcNAcβ-SCH$_2$CH$_2$CONHCH$_2$NHCOCH=CH$_2$ (35 mg, 69%) was obtained.

WORKING EXAMPLE 19

To 4,5-dihydro-2-methyl{1,2-dideoxy-4-O-(β-D-galactopyranosyl)-α-D-glucopyranosyl}[2,1-d]oxazole (18 mg, 48 μmol) in a microtube was added a 0.05 M carbonate buffer (pH 10.4) solution (2.0 mL) of GlcNAc(β1-4)GlcNAcβ-SCH$_2$CH$_2$CONHCH$_2$NHCOCH=CH$_2$ (19 mg, 32 μmol) and chitinase (Bacillus sp., 70.4 mU), and the resultant mixture was incubated for two hours at 40° C. The enzyme was inactivated by heating the resulting mixture for 20 minutes at 90° C. After distilling off the solvent and dissolving the residue in water, the mixture was refined by HPLC fractionation (Inertsil-ODS, H$_2$O/MeOH=900:7, 5.0 mL/min), and Gal(β1-4)GlcNAc(β1-4)GlcNAc(β1-4)GlcNAcβ-SCH$_2$CH$_2$CONHCH$_2$NHCOCH=CH$_2$ (17 mg, 54%) was obtained.

The corresponding glycosides can be synthesized with mutant chitinase, endo-β-N-acetylglucosaminidase M, and endo-β-N-acetylglucosaminidase A from sugar oxazoline derivatives in the same way as above.

WORKING EXAMPLE 20

Figure 20:
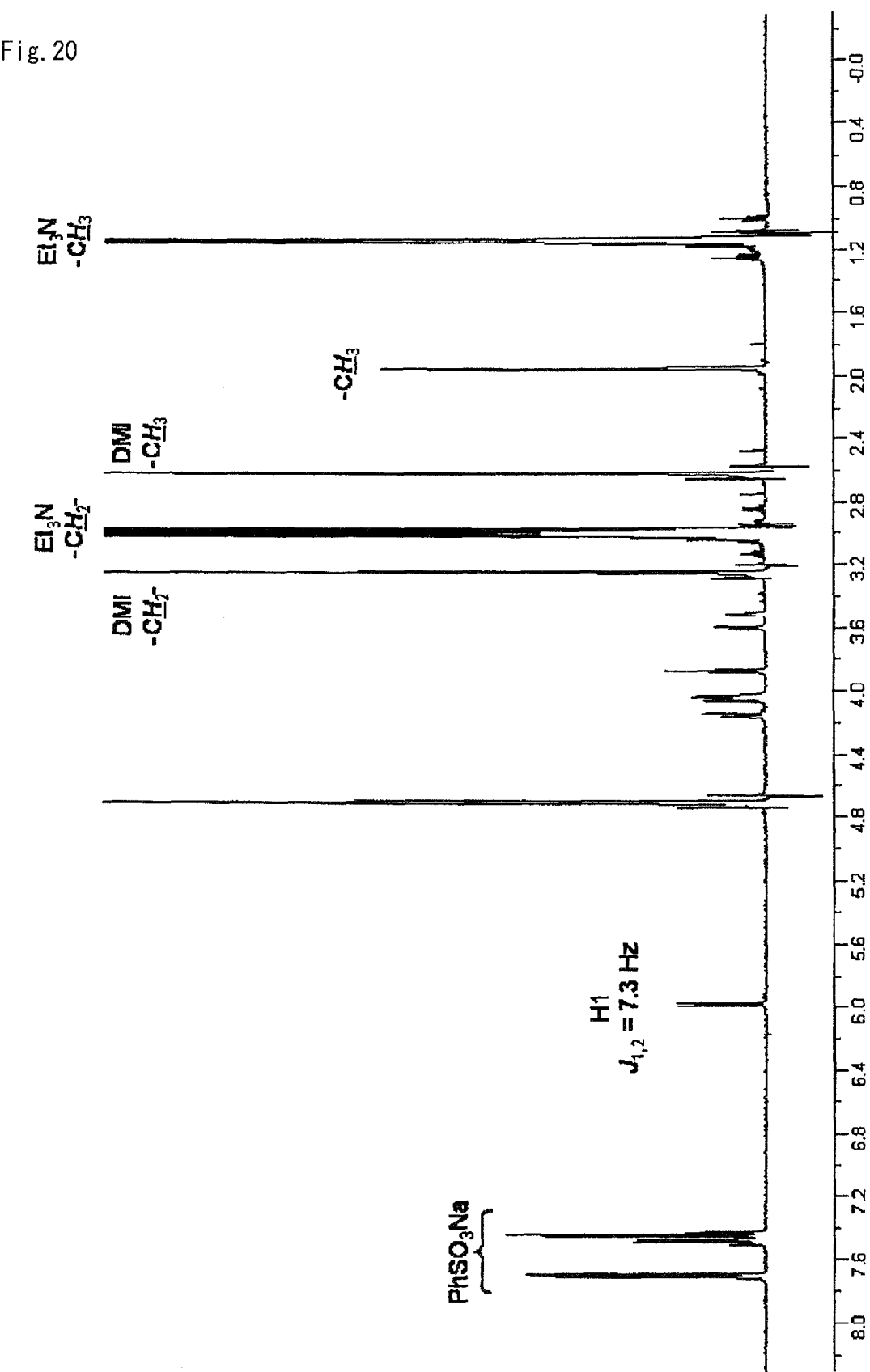
FIG. 20 is the $^1$H-NMR spectrum of the product sodium 2-methyl(1,2-dideoxy-α-D-glucopyrano)[2,1-d]-2-oxazoline-6-sulfate-containing reaction solution obtained in Working Example 20, wherein DMI is 1,3-dimethyl-2-imidazolidinone, Et$_3$N is triethylamine, and PhSO$_3$Na is sodium benzenesulfonate.

To 3.2 mg (18.75 μmol) of 2-chloro-1,3-dimethylimidazolinium chloride was added 2.0 mg (6.25 μmol) of sodium N-acetylglucosamine-6-sulfate, 7.8 μL (56.25 μmol) of triethylamine, and 50 μL of deuterated water and the resultant mixture was stirred for 15 minutes at 0° C. When this reaction solution was analyzed by NMR after addition of 400 μL of deuterated water, it was verified that the product, sodium 2-methyl(1,2-dideoxy-α-D-glucopyrano)[2,1-d]-2-oxazoline-6-sulfate, was obtained (yield: 84%). The yield of the product was calculated from the area ratio of the $^1$H-NMR spectrum after adding sodium benzenesulfonate to the reaction solution as a reference standard. FIG. 20 shows the $^1$H-NMR spectrum of the reaction solution containing the product sodium 2-methyl(1,2-dideoxy-α-D-glucopyrano)[2,1-d]-2-oxazoline-6-sulfate obtained.

WORKING EXAMPLE 21

Figure 21:
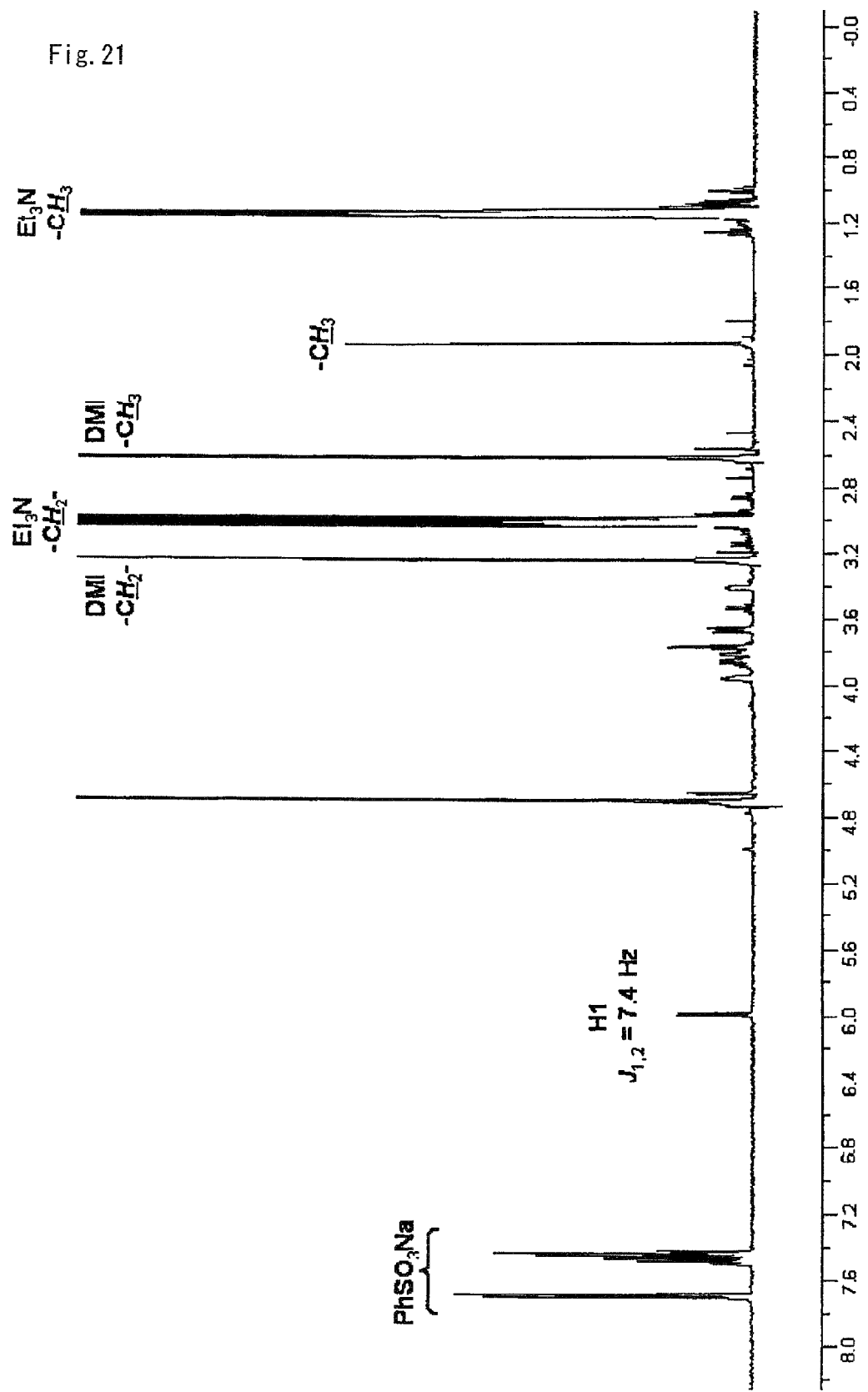
FIG. 21 is the $^1$H-NMR spectrum of the product disodium 2-methyl(1,2-dideoxy-α-D-glucopyrano)[2,1-d]-2-oxazoline-6-phosphate-containing reaction solution obtained in Working Example 21, wherein DMI is 1,3-dimethyl-2-imidazolidinone, Et$_3$N is triethylamine, and PhSO$_3$Na is sodium benzenesulfonate.

To 3.2 mg (18.75 μmol) of 2-chloro-1,3-dimethylimidazolinium chloride was added 2.2 mg (6.25 μmol) of disodium N-acetylglucosamine-6-phosphate, 7.8 μL (56.25 μmol) of triethylamine, and 50 μL of deuterated water and the resultant mixture was stirred for 15 minutes at 0° C. When this reaction solution was analyzed by NMR after addition of 400 μL of deuterated water, it was verified that the product, disodium 2-methyl(1,2-dideoxy-α-D-glucopyrano)[2,1-d]-2-oxazoline-6-phosphate, was obtained (yield: 79%). The yield of the product was calculated from the area ratio of the $^1$H-NMR spectrum after adding sodium benzenesulfonate to the reaction solution as a reference standard. FIG. 21 shows the $^1$H-NMR spectrum of the reaction solution containing the product disodium 2-methyl(1,2-dideoxy-α-D-glucopyrano)[2,1-d]-2-oxazoline-6-phosphate obtained.

WORKING EXAMPLE 22

Figure 22:
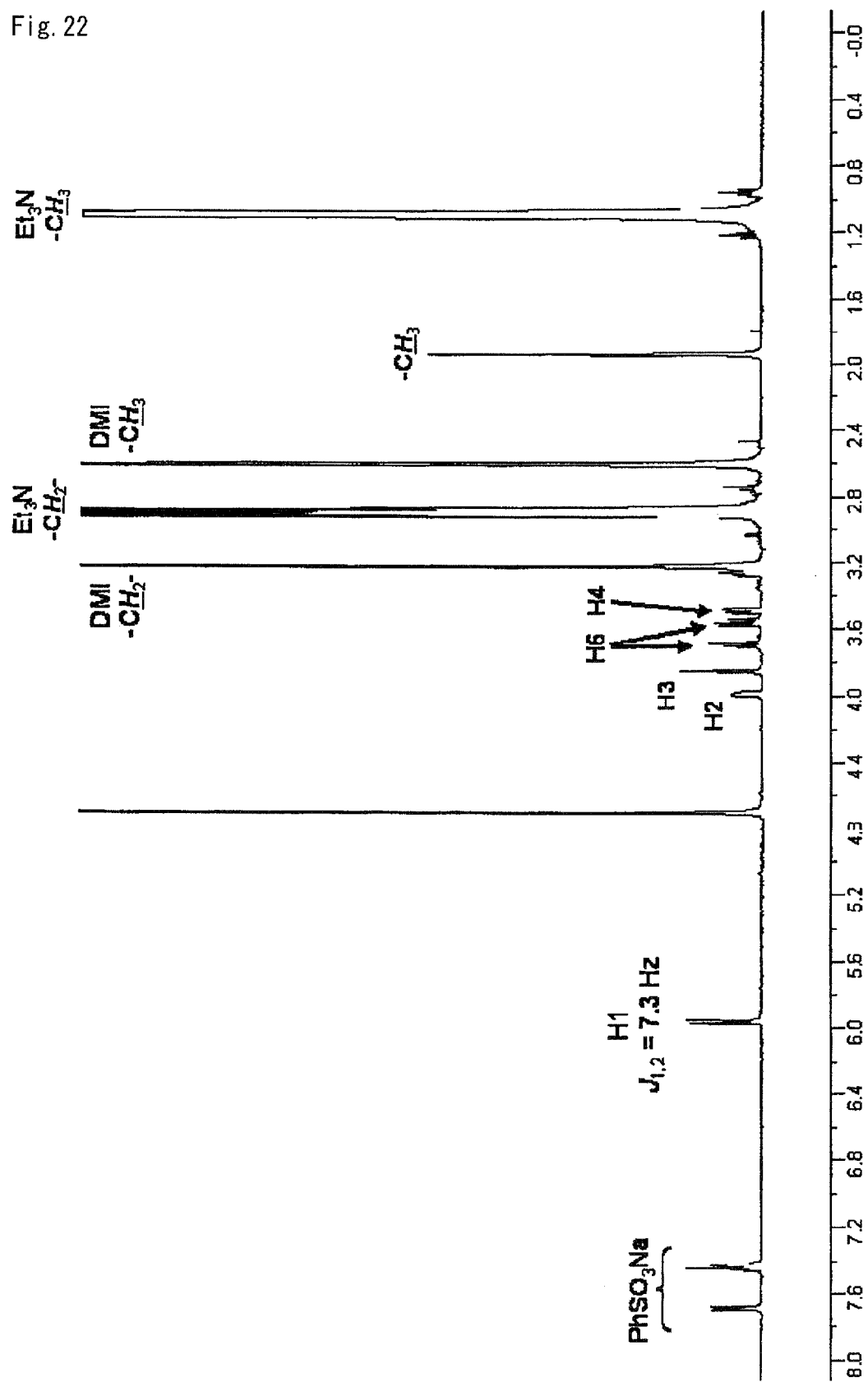
FIG. 22 is the $^1$H-NMR spectrum of the product 2-methyl (1,2-dideoxy-α-D-glucopyrano)[2,1-d]-2-oxazoline-containing reaction solution obtained in Working Example 22, wherein DMI is 1,3-dimethyl-2-imidazolidinone, Et$_3$N is triethylamine, and PhSO$_3$Na is sodium benzenesulfonate.

To 104.5 mg (0.375 mmol) of 2-chloro-1,3-dimethylimidazolinium hexafluorophosphate was added 27.7 mg (0.125 mmol) of N-acetylglucosamine, 156 μL (1.125 mmol) of triethylamine, and 500 μL of deuterated water and the resultant mixture was stirred for 15 minutes at room temperature. When this reaction solution was analyzed by NMR it was verified that the product, 2-methyl(1,2-dideoxy-α-D-glucopyrano)[2,1-d]-2-oxazoline, was obtained (yield: 82%). The yield of the product was calculated from the area ratio of the $^1$H-NMR spectrum after adding sodium benzenesulfonate to the reaction solution as a reference standard. FIG. 22 shows the $^1$H-NMR spectrum of the reaction solution containing the product 2-methyl(1,2-dideoxy-α-D-glucopyrano)[2,1-d]-2-oxazoline obtained.

WORKING EXAMPLE 23

Figure 23:
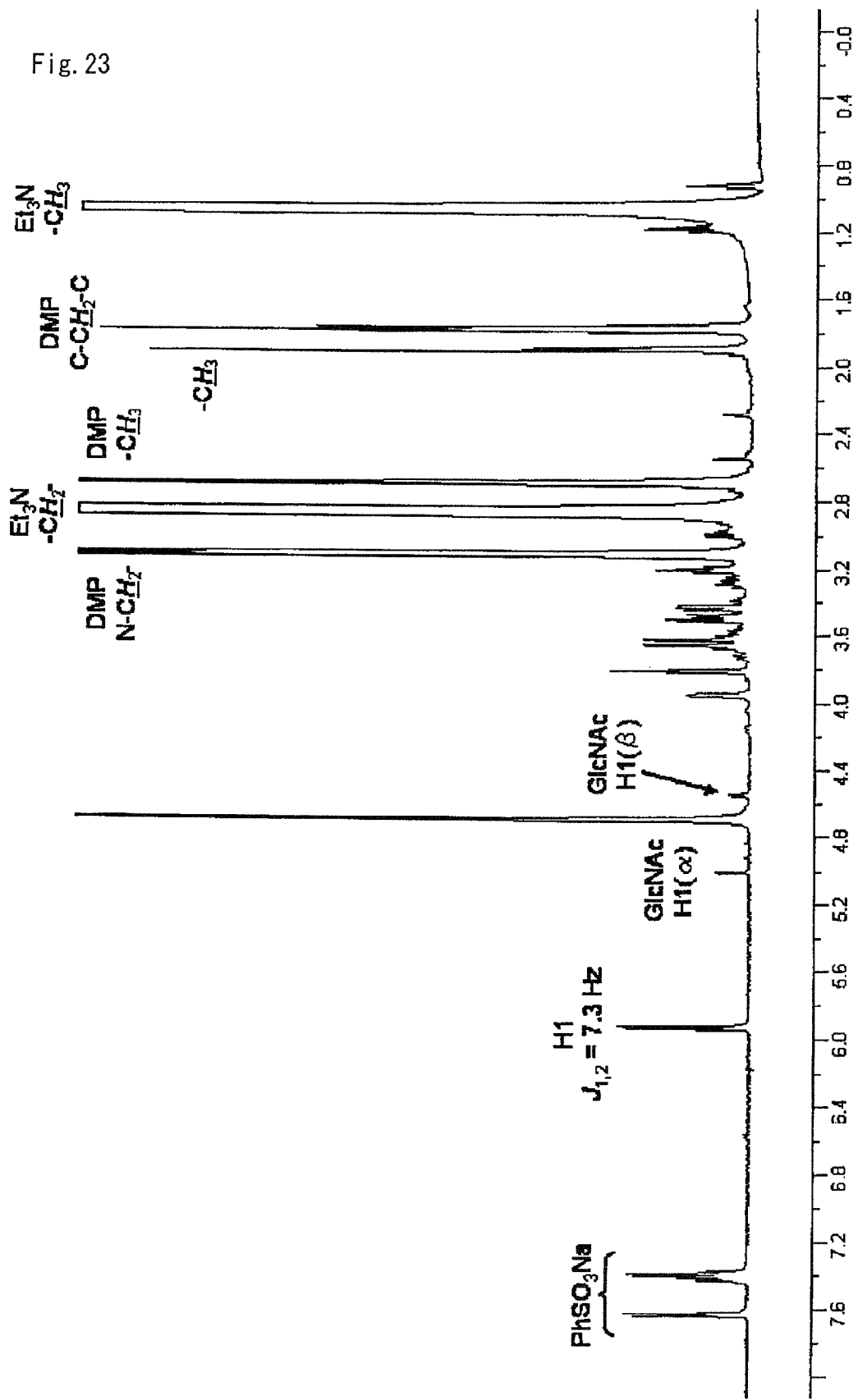
FIG. 23 is the $^1$H-NMR spectrum of the product 2-methyl (1,2-dideoxy-α-D-glucopyrano)[2,1-d]-2-oxazoline-containing reaction solution obtained in Working Example 23. DMP is 1,3-dimethyl-3,4,5,6-tetrahydro-2(1H)-pyrimidinone, Et$_3$N is triethylamine, PhSO$_3$Na is sodium benzenesulfonate, and GlcNAc is the starting material N-acetylglucosamine.

To 68.7 mg (0.375 mmol) of 2-chloro-1,3-dimethyl-3,4,5,6-tetrahydro-2(1H)-pyrimidinium chloride was added 27.7 mg (0.125 mmol) of N-acetylglucosamine, 156 μL (1.125 mmol) of triethylamine, and 500 μL of deuterated water and the resultant mixture was stirred for 3 hours at 0° C. When this reaction solution was analyzed by NMR, it was verified that the product, 2-methyl(1,2-dideoxy-α-D-glucopyrano)[2,1-d]-2-oxazoline, was obtained (yield: 65%). The yield of the product was calculated from the area ratio of the $^1$H-NMR spectrum after adding sodium benzenesulfonate to the reaction solution as a reference standard. FIG. 23 shows the $^1$H-NMR spectrum of the reaction solution containing the product 2-methyl(1,2-dideoxy-α-D-glucopyrano)[2,1-d]-2-oxazoline obtained.

WORKING EXAMPLE 24

Figure 24:
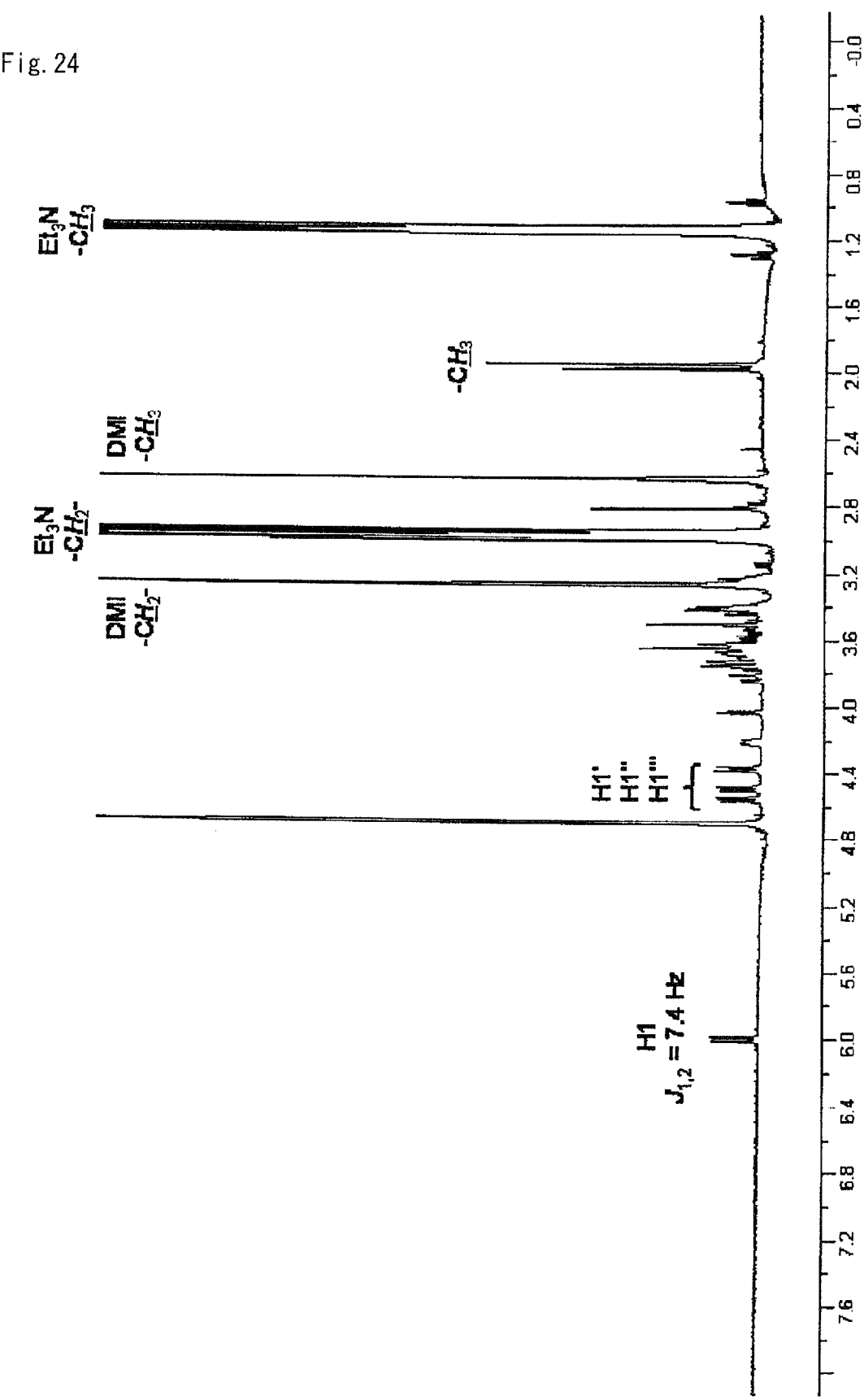
FIG. 24 is the $^1$H-NMR spectrum of the product 2-methyl [3-O-[4-O-[β-O-(β3-D-glucuronopyranosyl)-2-acetamido-2-deoxy-β-D-glucopyranosyl]-β-D-glucuronopyranosyl]-1,2-dideoxy-α-D-glucopyrano][2,1-d]-2-oxazoline-containing reaction solution obtained in Working Example 24, wherein DMI is 1,3-dimethyl-2-imidazolidinone, and Et$_3$N is triethylamine.

To 5.3 mg (31.25 μmol) of 2-chloro-1,3-dimethylimidazolinium chloride was added 4.9 mg (6.25 μmol) of hyaluronic acid tetrasaccharide, 13.9 μL (93.75 μmol) of triethylamine, and 50 μL of deuterated water and the resultant mixture was stirred for 30 minutes at 0° C. When this reaction solution was analyzed by NMR after addition of 400 μL of deuterated water, it was verified that the product, 2-methyl[3-O-[4-O-[3-O-(β-D-glucuronopyranosyl)-2-acetamido-2-deoxy-β-D-glucopyranosyl]-β-D-glucuronopyranosyl]-1,2-dideoxy-α-D-glucopyrano][2,1-d]-2-oxazoline, was obtained (yield: quant.). The yield of the product was taken to be quantitative (quant.) because no peak of an anomer proton of the starting material hyaluronic acid tetrasaccharide was observed by NMR analysis of the reaction solution. FIG. 24 shows the $^1$H-NMR spectrum of the reaction solution containing the product 2-methyl[3-O-[4-O-[3-O-(β-D-glucuronopyranosyl)-2-acetamido-2-deoxy-β-D-glucopyranosyl]-β-D-glucuronopyranosyl]-1,2-dideoxy-α-D-glucopyrano][2,1-d]-2-oxazoline obtained.

WORKING EXAMPLE 25

To 85.8 mg (0.508 mmol) of 2-chloro-1,3-dimethylimidazolinium chloride was added 99.2 mg of an oligosaccharide of the following formula (5):

[Chemical Formula 25]

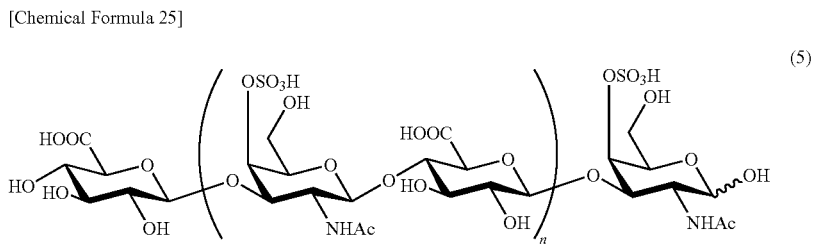

(5)

0.21 mL (1.50 mmol) of triethylamine, and 1.0 mL of deuterated water and the resultant mixture was allowed to stand for 30 minutes at 22° C. Analysis of this reaction solution by NMR confirmed that the oxazoline derivative of the following formula (6):

[Chemical Formula 26]

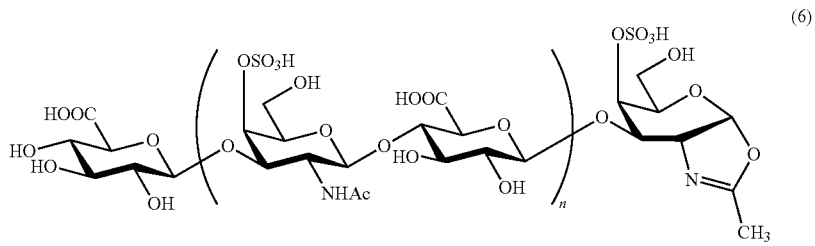

Figure 25:
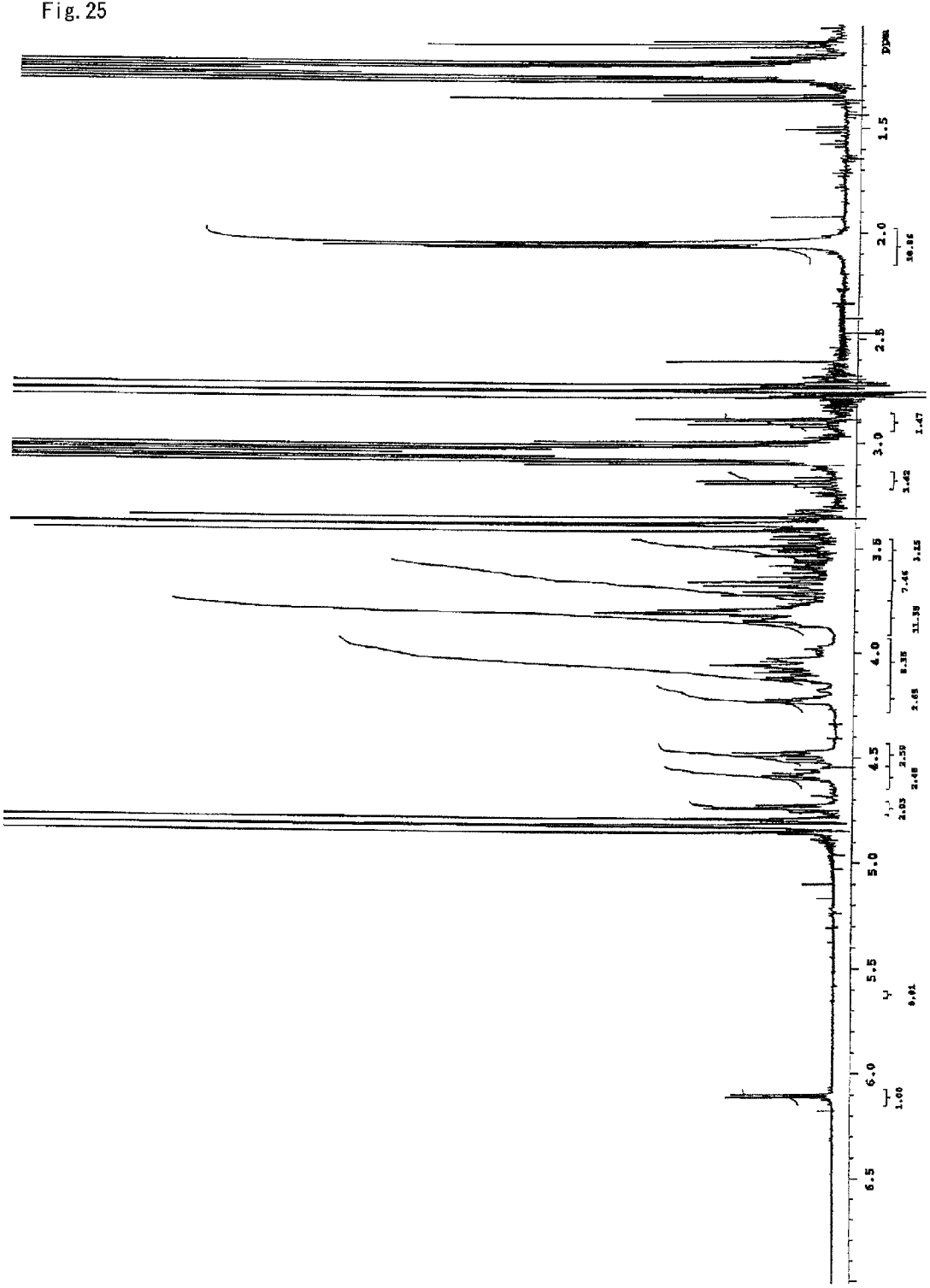
FIG. 25 is the $^1$H-NMR spectrum of the product-containing reaction solution obtained in Working Example 25.

(6)

was obtained quantitatively from the NMR heuristics, in the same manner as in Working Example 24. FIG. 25 shows the $^1$H-NMR spectrum of the reaction solution containing the target compound.

WORKING EXAMPLE 26

To 84.9 mg (0.502 mmol) of 2-chloro-1,3-dimethylimidazolinium chloride was added 95.9 mg of an oligosaccharide of the following formula (7):

[Chemical Formula 27]

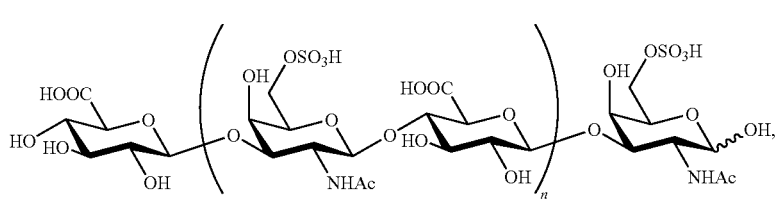

(7)

0.21 mL (1.50 mmol) of triethylamine, and 1.0 mL of deuterated water and the resultant mixture was allowed to stand for 30 minutes at 22° C. Analysis of this reaction solution by NMR confirmed that the oxazoline derivative of the following formula (8):

[Chemical Formula 28]

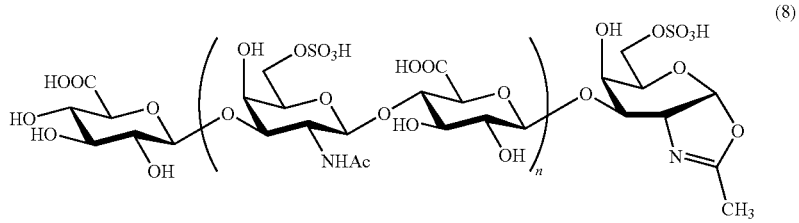

Figure 26:
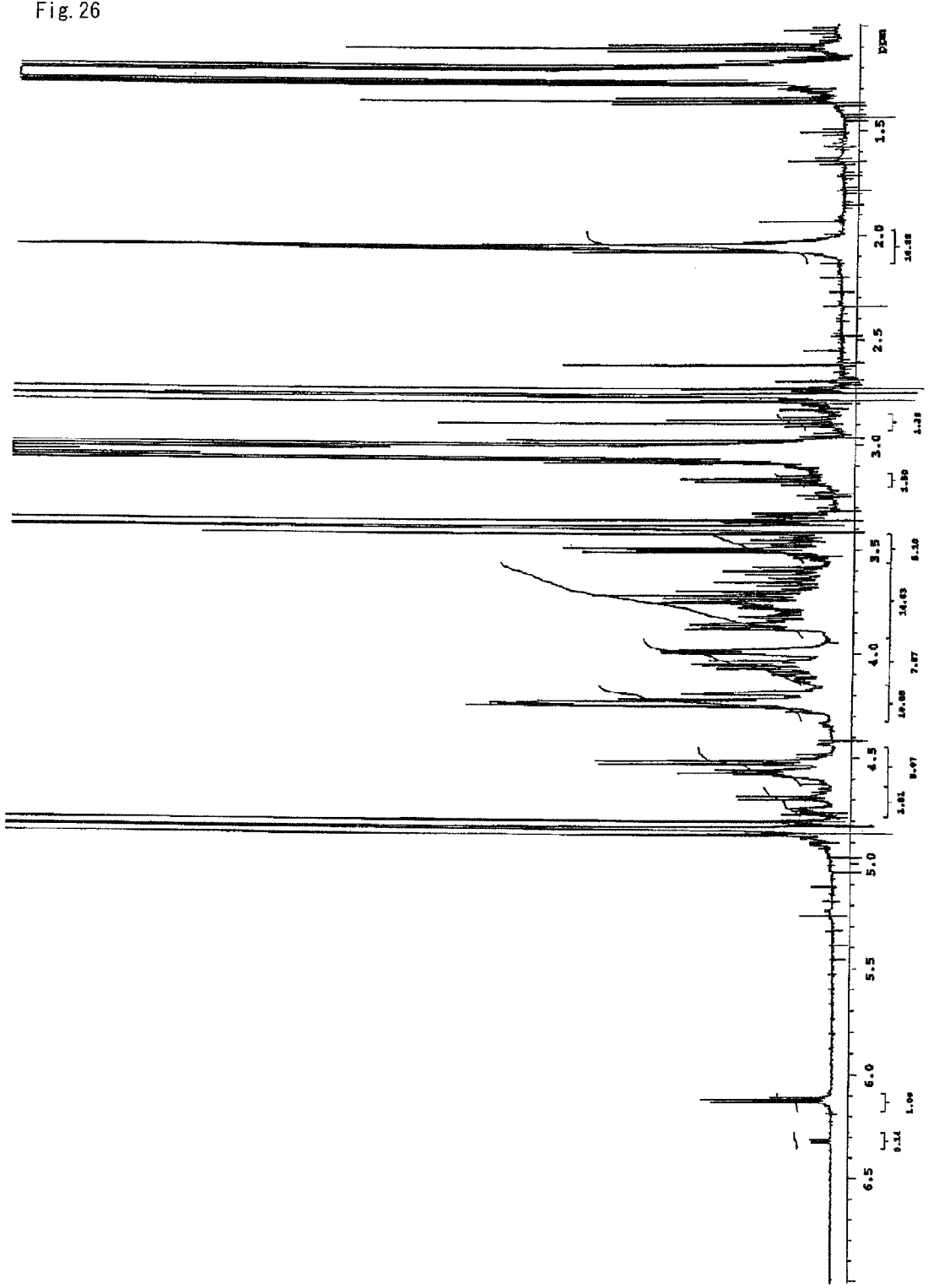
FIG. 26 is the $^1$H-NMR spectrum of the product-containing reaction solution obtained in Working Example 26.

(8)

was obtained quantitatively from the NMR heuristics, in the same manner as in Working Example 24. FIG. 26 shows the $^1$H-NMR spectrum of the reaction solution containing the target compound.

WORKING EXAMPLE 27

To a mixture solution of 20 mg of the oxazoline derivative of the formula (6) (obtained in Working Example 25) dissolved in 400 μL of 0.05 M sodium phosphate buffer (pH 7.3) was added hyaluronidase (from bovine testes, 700 U), and the resultant mixture was allowed to stand for 1, 2, 4, 6, or 72 hours at 30° C. The enzyme was inactivated by boiling the resulting mixture, and it was separated by HPLC after being diluted with water. It was confirmed as a result that the oxazoline derivative of the formula (6) polymerizes and grows over time.

WORKING EXAMPLE 28

To a mixture solution of 20 mg of the oxazoline derivative of the formula (8) (obtained in Working Example 26) dissolved in 400 μL of 0.05 M sodium phosphate buffer (pH 7.3) was added hyaluronidase (from bovine testes, 700 U), and the resultant mixture was allowed to stand for 1, 2, 4, 6, or 72 hours at 30° C. The enzyme was inactivated by boiling the mixture obtained, and it was separated by HPLC after being diluted with water. It was confirmed as a result that the oxazoline derivative shown by the formula (8) polymerizes and grows over time.

INDUSTRIAL APPLICABILITY

The present invention provides a simple process for producing an oxazoline derivative from an unprotected sugar and a process for the production of a glycoside compound which comprises using the oxazoline derivative product. In the present invention, the oxazoline derivatives of the sugar bearing a free hemiacetalic hydroxyl group and an amido group are synthesized with formamidine derivatives as dehydrating agents in one step in an aqueous solution, and the resultant oxazoline derivatives are used as sugar donors and subjected to a reaction with glycoside hydrolase to form glycoside compounds. The resulting glycoside compounds, that is sugar chain-added compounds or oligosaccharides, are useful for various applications in connection with, for example, bioactive oligosaccharides, carriers for drug delivery systems, surfactants, glycopharmaceuticals, glycopeptides, glycoproteins, glycopolymers, and others. The products glycoside compounds are useful in researches on cell recognition, immunity, cell differentiation, cell migration, fertilization, maturation, tissue morphogenesis, inflammation, wound healing, cancer metastasis, tumorigenesis, and the like.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

The invention claimed is:

1. A process for producing an oxazoline derivative of the general formula (3) in an aqueous solvent:

[Chemical Formula 3]

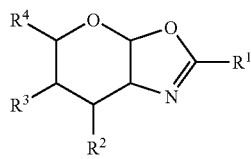

(3)

wherein $R^1$ is an alkyl group; $R^2$, $R^3$, and $R^4$ may be identical or different from one another, $R^2$ and $R^3$ are each independently selected from the group consisting of a hydrogen atom, a hydroxyl group, a hydroxymethyl group, an acetamido group, a carboxy group, a sulfuric acid residue, a phosphoric acid residue, and a sugar residue, and $R^4$ is selected from the group consisting of a hydrogen atom, a hydroxyl group, a hydroxymethyl group, an acetamido group, a carboxy group, a sulfuric acid residue, a phosphoric acid residue, a sugar residue, and a hydroxymethyl group modified by sulfation or phosphorylation, which comprises treating a sugar, with a hemiacetalic hydroxyl group and an amido group, of the general formula (1):

[Chemical Formula 1]

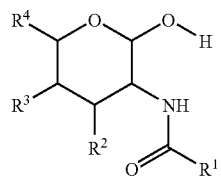

(1)

wherein $R^1$, $R^2$, $R^3$, and $R^4$ have the same meanings as defined above, with a haloformamidinium derivative of the general formula (2):

[Chemical Formula 2]

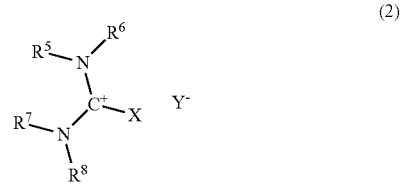

(2)

wherein $R^5$, $R^6$, $R^7$, and $R^8$, which may be identical or different one another, are each independently selected from the group consisting of an unsubstituted or optionally substituted alkyl group, an unsubstituted or optionally substituted alkenyl group, and an unsubstituted or optionally substituted aryl group; $R^5$ taken together with $R^7$, or $R^6$ taken together with $R^8$, may form a ring; or $R^5$ taken together with $R^6$, or $R^7$ taken together with $R^8$, may form a ring; X is a halogen atom; and $Y^-$ is an anion.

2. The process according to claim 1, wherein Y is a halogen atom, OH, $BF_4$, or $PF_6$, and the sugar of the general formula (1) is reacted with the haloformamidinium derivative of the general formula (2) in an aqueous solvent.

3. The process according to claim 1, wherein
(1) the sugar of the general formula (1) is selected from the group consisting of N-acetylglucosamine, N-acetylgalactosamine, and N-acetylmannosamine,
(2) the sugar of the general formula (1) is selected from the group consisting of N-acetyllactosamine, N,N'-diacetylchitobiose, hyaluronic acid disaccharide, and glycosaminoglycan disaccharide, or
(3) the sugar of the general formula (1) is selected from the group consisting of N-linked glycoprotein saccharides, O-linked glycoprotein saccharides, and chitooligosaccharides.

4. A process for producing a glycoside compound which comprises treating a sugar, with a hemiacetalic hydroxyl group and an amido group, of the general formula (1) in an aqueous solvent:

[Chemical Formula 4]

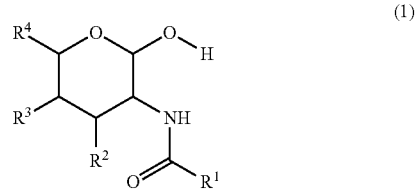

(1)

wherein $R^1$ is an alkyl group, $R^2$, $R^3$, and $R^4$ may be identical or different from one another, $R^2$ and $R^3$ are each independently selected from the group consisting of a hydrogen atom, a hydroxyl group, a hydroxymethyl group, an acetamido group, a carboxy group, a sulfuric acid residue, a phosphoric acid residue, or a sugar residue and $R^4$ is selected from the group consisting of a hydrogen atom, a hydroxyl group, a hydroxymethyl group, an acetamido group, a carboxy group, a sulfuric acid residue, a phosphoric acid residue, a sugar residue, and a hydroxymethyl group modified by sulfation or phosphorylation, with a haloformamidinium derivative of the general formula (2):

[Chemical Formula 5]

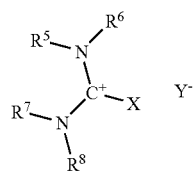

(2)

wherein $R^5$, $R^6$, $R^7$, and $R^8$, which may be identical or different one another, are each independently selected from the group consisting of an unsubstituted or optionally substituted alkyl group, an unsubstituted or optionally substituted alkenyl group, and an unsubstituted or optionally substituted aryl group; $R^5$ taken together with $R^7$, or $R^6$ taken together with $R^8$, may form a ring; or $R^5$ taken together with $R^6$, or $R^7$ taken together with $R^8$, may form a ring; X is a halogen atom; and $Y^-$ is an anion, to form an oxazoline derivative of the general formula (3):

[Chemical Formula 6]

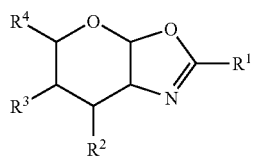

(3)

wherein $R^1$, $R^2$, $R^3$, and $R^4$ have the same meanings as defined above, and then contacting the resulting oxazoline derivative of the general formula (3), used as a sugar donor, with glycosyltransferase or glycoside hydrolase in the presence of a sugar acceptor to form a sugar chain-added compound.

5. The process according to claim 4, wherein the glycosyltransferase or glycoside hydrolase is selected from the group consisting of chitinase, mutant chitinase, endo-β-N-acetylglucosaminidase M, endo-β-N-acetylglucosaminidase A, hyaluronidase, and chondroitinase.

6. The process according to claim 4, wherein
(1) the sugar of the general formula (1) is selected from the group consisting of N-acetylglucosamine, N-acetylgalactosamine, and N-acetylmannosamine,
(2) the sugar of the general formula (1) is selected from the group consisting of N-acetyllactosamine, N,N'-diacetylchitobiose, hyaluronic acid disaccharide, and glycosaminoglycan disaccharide, or
(3) the sugar of the general formula (1) is selected from the group consisting of N-linked glycoprotein saccharides, O-linked glycoprotein saccharides, and chitooligosaccharides.

7. The process according to claim 2, wherein
(1) the sugar of the general formula (1) is selected from the group consisting of N-acetylglucosamine, N-acetylgalactosamine, and N-acetylmannosamine,
(2) the sugar of the general formula (1) is selected from the group consisting of N-acetyllactosamine, N,N'-diacetylchitobiose, hyaluronic acid disaccharide, and glycosaminoglycan disaccharide, or
(3) the sugar of the general formula (1) is selected from the group consisting of N-linked glycoprotein saccharides, O-linked glycoprotein saccharides, and chitooligosaccharides.

8. The process according to claim 5, wherein
(1) the sugar of the general formula (1) is selected from the group consisting of N-acetylglucosamine, N-acetylgalactosamine, and N-acetylmannosamine,
(2) the sugar of the general formula (1) is selected from the group consisting of N-acetyllactosamine, N,N'-d iacetylchitobiose, hyaluronic acid disaccharide, and glycosaminoglycan disaccharide, or
(3) the sugar of the general formula (1) is selected from the group consisting of N-linked glycoprotein saccharides, O-linked glycoprotein saccharides, and chitooligosaccharides.

* * * * *

UNITED STATES PATENT AND TRADEMARK OFFICE
CERTIFICATE OF CORRECTION

PATENT NO. : 8,470,986 B2
APPLICATION NO. : 12/528547
DATED : June 25, 2013
INVENTOR(S) : Shoda et al.

Page 1 of 1

It is certified that error appears in the above-identified patent and that said Letters Patent is hereby corrected as shown below:

In the Claims

Claim 8, Col. 36, lines 35-36, "N,N'-d iacetylchitobiose" should be --N,N'-diacetylchitobiose--.

Signed and Sealed this
Twenty-sixth Day of August, 2014

Michelle K. Lee
*Deputy Director of the United States Patent and Trademark Office*